(12) United States Patent
Olson et al.

(10) Patent No.: US 11,647,935 B2
(45) Date of Patent: May 16, 2023

(54) MASKED RING ELECTRODES

(71) Applicant: St. Jude Medical, Cardiology Division, Inc., St. Paul, MN (US)

(72) Inventors: Gregory K. Olson, Elk River, MN (US); Travis Dahlen, Forest Lake, MN (US); Brian M. Monahan, Elk River, MN (US); Loell B. Moon, Ham Lake, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 668 days.

(21) Appl. No.: 16/042,336

(22) Filed: Jul. 23, 2018

(65) Prior Publication Data

US 2019/0021620 A1  Jan. 24, 2019

Related U.S. Application Data

(60) Provisional application No. 62/536,369, filed on Jul. 24, 2017.

(51) Int. Cl.
*A61B 18/00* (2006.01)
*A61B 18/14* (2006.01)
(Continued)

(52) U.S. Cl.
CPC .............. *A61B 5/283* (2021.01); *A61B 5/287* (2021.01); *A61B 5/6858* (2013.01);
(Continued)

(58) Field of Classification Search
CPC ....... A61B 5/0422; A61B 5/283; A61B 5/287; A61B 5/6858; A61B 18/1492;
(Continued)

(56) References Cited

U.S. PATENT DOCUMENTS 4,522,212 A   6/1985 Gelinas et al.
4,690,155 A * 9/1987 Hess .................... A61B 5/0422
                                                607/122
(Continued)

FOREIGN PATENT DOCUMENTS

AU    2015202258 B2   6/2016
AU    2016204351 A1   1/2017
(Continued)

*Primary Examiner* — Adam Z Minchella
(74) *Attorney, Agent, or Firm* — Kilpatrick Townsend & Stockton LLP

(57) ABSTRACT

A partially-masked electrode includes a conductive material and an insulated coating having an outer surface. The insulated coating defines a contoured opening that exposes or reveals an area of the conductive material, wherein the contoured opening has an upper perimeter at the outer surface of the insulated coating. When the upper perimeter of the insulated surface coating is placed in contact with a tissue of interest, wherein the tissue of interest is proximate a blood pool, the insulated coating creates a seal between the blood pool and the contoured opening so that no blood in the blood pool can contact the conductive material. This seal reduces or eliminates the reception of far field effects in the blood pool by the electrode, making it easier to locate and diagnose unhealthy tissue.

19 Claims, 20 Drawing Sheets

(51) Int. Cl.
*A61B 5/283* (2021.01)
*A61B 5/00* (2006.01)
*A61N 1/05* (2006.01)
*A61B 5/287* (2021.01)

(52) U.S. Cl.
CPC .......... *A61B 18/1492* (2013.01); *A61N 1/056* (2013.01); *A61B 5/4848* (2013.01); *A61B 2018/00071* (2013.01); *A61B 2018/00083* (2013.01); *A61B 2018/00107* (2013.01); *A61B 2018/00267* (2013.01); *A61B 2018/00357* (2013.01); *A61B 2018/00363* (2013.01); *A61B 2018/00839* (2013.01); *A61B 2018/1497* (2013.01)

(58) Field of Classification Search
CPC ........ A61B 5/4848; A61B 2018/00071; A61B 2018/00083; A61B 2018/00107; A61B 2018/00267; A61B 2018/00357; A61B 2018/00363; A61B 2018/00839; A61B 2018/1497; A61N 1/056
See application file for complete search history.

(56) References Cited

U.S. PATENT DOCUMENTS

| | | | |
|---|---|---|---|
| 4,847,980 A * | 7/1989 | Witkowski | A61B 5/042 29/592.1 |
| 5,029,585 A * | 7/1991 | Lieber | A61B 5/0215 600/396 |
| 5,224,939 A | 7/1993 | Holman et al. | |
| 5,380,301 A | 1/1995 | Prichard et al. | |
| 5,400,783 A | 3/1995 | Pomeranz et al. | |
| 5,456,254 A | 10/1995 | Pietroski et al. | |
| 5,626,136 A | 5/1997 | Webster, Jr. | |
| 5,643,255 A | 7/1997 | Organ | |
| 5,702,438 A | 12/1997 | Avitall | |
| 5,715,817 A | 2/1998 | Stevens-Wright et al. | |
| 5,715,832 A | 2/1998 | Koblish et al. | |
| 5,772,590 A * | 6/1998 | Webster, Jr. | A61B 5/0422 600/374 |
| 5,827,278 A | 10/1998 | Webster, Jr. | |
| 5,876,373 A | 3/1999 | Giba et al. | |
| 5,964,757 A | 10/1999 | Ponzi | |
| 6,029,091 A | 2/2000 | de la Rama et al. | |
| 6,071,282 A | 6/2000 | Fleischman | |
| 6,074,379 A | 6/2000 | Prichard | |
| 6,123,699 A | 9/2000 | Webster, Jr. | |
| 6,171,277 B1 | 1/2001 | Ponzi | |
| 6,183,463 B1 | 2/2001 | Webster, Jr. | |
| 6,198,974 B1 | 3/2001 | Webster, Jr. | |
| 6,210,407 B1 | 4/2001 | Webster | |
| 6,267,746 B1 | 7/2001 | Bumbalough | |
| 6,273,404 B1 | 8/2001 | Holman et al. | |
| 6,415,187 B1 | 7/2002 | Kuzma et al. | |
| 6,491,681 B1 | 12/2002 | Kunis et al. | |
| 6,522,932 B1 | 2/2003 | Kuzma et al. | |
| 6,554,794 B1 | 4/2003 | Mueller et al. | |
| 6,652,515 B1 | 11/2003 | Maguire et al. | |
| 6,658,302 B1 | 12/2003 | Kuzma et al. | |
| 6,692,492 B2 * | 2/2004 | Simpson | A61B 18/1492 606/41 |
| 6,837,886 B2 | 1/2005 | Collins et al. | |
| 6,961,602 B2 | 11/2005 | Fuimaono et al. | |
| 7,004,937 B2 | 2/2006 | Lentz et al. | |
| 7,027,851 B2 | 4/2006 | Mejia | |
| 7,089,045 B2 | 8/2006 | Fuimaono et al. | |
| 7,099,712 B2 | 8/2006 | Fuimaono et al. | |
| 7,214,220 B2 | 5/2007 | McGlinch et al. | |
| 7,217,256 B2 | 5/2007 | Di Palma | |
| 7,228,164 B2 | 6/2007 | Fuimaono et al. | |
| 7,255,695 B2 | 8/2007 | Falwell et al. | |
| 7,257,435 B2 | 8/2007 | Plaza | |
| 7,306,594 B2 | 12/2007 | Collins et al. | |
| 7,412,274 B2 | 8/2008 | Mejia | |
| 7,429,261 B2 | 9/2008 | Kunis et al. | |
| 7,561,907 B2 | 7/2009 | Fuimaono et al. | |
| 7,608,063 B2 | 10/2009 | Le et al. | |
| 7,625,365 B2 | 12/2009 | McGlinch et al. | |
| 7,666,204 B2 | 2/2010 | Thornton et al. | |
| 7,959,601 B2 | 6/2011 | McDaniel et al. | |
| 7,985,215 B2 | 7/2011 | Guo et al. | |
| 8,103,327 B2 | 1/2012 | Harlev et al. | |
| 8,137,321 B2 | 3/2012 | Argentine | |
| 8,157,796 B2 | 4/2012 | Collins et al. | |
| 8,221,390 B2 | 7/2012 | Pal et al. | |
| 8,224,416 B2 | 7/2012 | de la Rama et al. | |
| 8,271,099 B1 | 9/2012 | Swanson | |
| 8,273,016 B2 | 9/2012 | O'sullivan | |
| 8,376,990 B2 | 2/2013 | Ponzi et al. | |
| 8,391,947 B2 | 3/2013 | Urman et al. | |
| 8,447,377 B2 | 5/2013 | Harlev et al. | |
| 8,486,063 B2 | 7/2013 | Werneth et al. | |
| 8,560,086 B2 | 10/2013 | Just et al. | |
| 8,565,894 B2 | 10/2013 | Vetter et al. | |
| 8,603,069 B2 | 12/2013 | Selkie | |
| 8,608,703 B2 | 12/2013 | Riles et al. | |
| 8,649,880 B1 | 2/2014 | Parker, Jr. | |
| 8,700,120 B2 | 4/2014 | Koblish | |
| 8,700,129 B2 | 4/2014 | Hauck et al. | |
| 8,706,193 B2 | 4/2014 | Govari et al. | |
| 8,744,599 B2 | 6/2014 | Tegg | |
| 8,755,861 B2 | 6/2014 | Harlev et al. | |
| 8,777,929 B2 | 7/2014 | Schneider et al. | |
| 8,792,962 B2 | 7/2014 | Esguerra et al. | |
| 8,814,824 B2 | 8/2014 | Kauphusman et al. | |
| 8,814,825 B2 | 8/2014 | Tegg et al. | |
| 8,882,705 B2 | 11/2014 | McDaniel et al. | |
| 8,894,610 B2 | 11/2014 | Macnamara et al. | |
| 8,996,091 B2 | 3/2015 | de la Rama et al. | |
| 9,017,308 B2 | 4/2015 | Klisch et al. | |
| 9,033,917 B2 | 5/2015 | Magana et al. | |
| 9,044,245 B2 | 6/2015 | Condie et al. | |
| 9,050,010 B2 | 6/2015 | Bui et al. | |
| 9,101,733 B2 | 8/2015 | McDaniel | |
| 9,204,929 B2 | 12/2015 | Solis | |
| 9,216,056 B2 | 12/2015 | Datta et al. | |
| 9,247,990 B2 | 2/2016 | Kauphusman et al. | |
| 9,326,815 B2 | 5/2016 | Watson | |
| 9,339,331 B2 | 5/2016 | Tegg et al. | |
| 9,339,631 B2 | 5/2016 | Graham et al. | |
| 9,433,751 B2 | 9/2016 | Ponzi et al. | |
| 9,433,752 B2 | 9/2016 | Jimenez et al. | |
| 9,468,495 B2 | 10/2016 | Kunis et al. | |
| 9,486,280 B2 | 11/2016 | Koblish et al. | |
| 9,486,282 B2 | 11/2016 | Solis | |
| 9,539,413 B2 | 1/2017 | Ogle | |
| 9,649,158 B2 | 5/2017 | Datta et al. | |
| 9,687,166 B2 | 6/2017 | Subramaniam et al. | |
| 9,693,733 B2 | 7/2017 | Altmann et al. | |
| 9,694,159 B2 | 7/2017 | Schneider et al. | |
| 9,694,161 B2 | 7/2017 | Selkee | |
| 9,788,895 B2 | 10/2017 | Solis | |
| 9,820,664 B2 | 11/2017 | Hoitink et al. | |
| 9,844,645 B2 | 12/2017 | Pai et al. | |
| 9,848,795 B2 | 12/2017 | Marecki et al. | |
| 9,872,717 B2 * | 1/2018 | Bencini | A61B 18/02 |
| 9,907,480 B2 | 3/2018 | Basu et al. | |
| 9,919,132 B2 | 3/2018 | Tegg et al. | |
| 9,949,656 B2 | 4/2018 | Wu et al. | |
| 9,986,949 B2 | 6/2018 | Govari et al. | |
| 10,004,877 B2 | 6/2018 | Tegg | |
| 10,034,637 B2 | 7/2018 | Harlev et al. | |
| 10,052,457 B2 | 8/2018 | Nguyen et al. | |
| 10,065,019 B2 | 9/2018 | Hamuro et al. | |
| 10,099,036 B2 | 10/2018 | Heideman et al. | |
| 10,118,022 B2 | 11/2018 | Helgeson et al. | |
| 10,143,394 B2 | 12/2018 | Solis | |
| 10,285,610 B2 | 5/2019 | Wu | |
| 10,322,261 B2 | 6/2019 | Pai et al. | |
| 10,362,952 B2 | 7/2019 | Basu et al. | |
| 10,362,954 B2 | 7/2019 | de la Rama et al. | |
| 10,376,170 B2 | 8/2019 | Quinn et al. | |

(56) References Cited

U.S. PATENT DOCUMENTS

| | | |
|---|---|---|
| 10,384,036 B2 | 8/2019 | Romoscanu |
| 10,398,500 B2 | 9/2019 | Huszar et al. |
| 10,478,325 B2 | 11/2019 | Syed |
| 10,506,938 B2 | 12/2019 | Wu et al. |
| 10,537,259 B2 | 1/2020 | Wu et al. |
| 10,542,899 B2 | 1/2020 | Wu et al. |
| 10,556,091 B2 | 2/2020 | Truhler et al. |
| 10,575,742 B2 | 3/2020 | Wu et al. |
| 10,575,745 B2 | 3/2020 | Solis |
| 10,578,737 B2 | 3/2020 | Gliner et al. |
| 10,595,738 B2 | 3/2020 | Sterrett et al. |
| 10,595,740 B2 | 3/2020 | Hoitink et al. |
| 10,602,948 B2 | 3/2020 | Wu et al. |
| 10,646,692 B2 | 5/2020 | Tegg et al. |
| 10,653,423 B2 | 5/2020 | Starnes |
| 10,702,177 B2 | 7/2020 | Aujla |
| 10,702,677 B2 | 7/2020 | Okamura et al. |
| 10,737,060 B2 | 8/2020 | Gupta et al. |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,912,925 B2 | 2/2021 | Houck |
| 10,953,196 B2 | 3/2021 | Raab et al. |
| 10,966,623 B2 | 4/2021 | Wu et al. |
| 10,966,753 B2 | 4/2021 | Coyle et al. |
| 10,967,150 B2 | 4/2021 | Helgeson et al. |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,083,400 B2 | 8/2021 | Hoitink et al. |
| 11,116,436 B2 | 9/2021 | Wu et al. |
| 11,116,476 B2 | 9/2021 | Buesseler et al. |
| 11,141,568 B2 | 10/2021 | Hsueh et al. |
| 11,160,482 B2 | 11/2021 | Solis |
| 11,172,858 B2 | 11/2021 | Olson et al. |
| 11,272,886 B2 | 3/2022 | Harlev et al. |
| 2001/0012918 A1* | 8/2001 | Swanson ............. A61B 5/6858 600/510 |
| 2002/0165484 A1 | 11/2002 | Bowe et al. |
| 2003/0212395 A1* | 11/2003 | Woloszko ........... A61B 18/149 606/41 |
| 2004/0162554 A1* | 8/2004 | Lee ..................... A61B 18/14 606/45 |
| 2004/0181139 A1* | 9/2004 | Falwell ............... A61B 5/6858 606/41 |
| 2005/0159741 A1 | 7/2005 | Paul et al. |
| 2007/0005053 A1 | 1/2007 | Dando |
| 2007/0299490 A1* | 12/2007 | Yang .................... A61N 1/056 607/116 |
| 2009/0198300 A1 | 8/2009 | Zhang et al. |
| 2010/0219085 A1* | 9/2010 | Oviatt, Jr. ........... A61B 5/1495 205/782 |
| 2011/0118726 A1 | 5/2011 | de la Rama et al. |
| 2011/0213231 A1 | 9/2011 | Hall et al. |
| 2012/0130220 A1* | 5/2012 | Maskara ............... A61B 5/287 600/374 |
| 2012/0143298 A1 | 6/2012 | Just et al. |
| 2012/0271302 A1 | 10/2012 | Behl et al. |
| 2012/0296232 A1 | 11/2012 | Ng |
| 2013/0172715 A1 | 7/2013 | Just et al. |
| 2013/0253504 A1 | 9/2013 | Fang |
| 2013/0274582 A1 | 10/2013 | Afonso et al. |
| 2014/0058197 A1* | 2/2014 | Salahieh ................ A61B 1/05 600/109 |
| 2014/0100639 A1 | 4/2014 | Lee et al. |
| 2014/0200639 A1 | 7/2014 | de la Rama |
| 2014/0296902 A1 | 10/2014 | Huszar et al. |
| 2014/0316496 A1 | 10/2014 | Masson et al. |
| 2014/0350564 A1 | 11/2014 | Huszar et al. |
| 2015/0080715 A1* | 3/2015 | Deno .................. A61B 34/20 600/424 |
| 2015/0105645 A1 | 4/2015 | Subramaniam et al. |
| 2015/0119911 A1 | 4/2015 | Mckenzie |
| 2015/0141785 A1 | 5/2015 | Hayam et al. |
| 2015/0159741 A1 | 6/2015 | Versteyhe et al. |
| 2015/0351652 A1 | 12/2015 | Marecki et al. |
| 2016/0143588 A1 | 5/2016 | Hoitink et al. |
| 2016/0213423 A1 | 7/2016 | Kauphusman et al. |
| 2016/0213916 A1 | 7/2016 | de la Rama |
| 2016/0278851 A1 | 9/2016 | Mannion et al. |
| 2016/0317094 A1 | 11/2016 | Byrd et al. |
| 2016/0331254 A1 | 11/2016 | Tegg et al. |
| 2016/0331933 A1 | 11/2016 | Knutsen |
| 2016/0374753 A1 | 12/2016 | Wu et al. |
| 2017/0000365 A1 | 1/2017 | Wu et al. |
| 2017/0042449 A1 | 2/2017 | Deno et al. |
| 2017/0100075 A1 | 4/2017 | Eliason et al. |
| 2017/0112404 A1 | 4/2017 | de la Rama et al. |
| 2017/0112405 A1 | 4/2017 | Sterrett et al. |
| 2017/0319269 A1 | 11/2017 | Oliverius et al. |
| 2017/0367756 A1 | 12/2017 | Sliwa et al. |
| 2018/0042667 A1 | 2/2018 | Pappone et al. |
| 2018/0050190 A1 | 2/2018 | Masson |
| 2018/0070845 A1 | 3/2018 | Hoitink et al. |
| 2018/0085064 A1 | 3/2018 | Auerbach et al. |
| 2018/0116539 A1 | 5/2018 | Olson et al. |
| 2018/0161093 A1 | 6/2018 | Basu et al. |
| 2018/0229030 A1 | 8/2018 | Dubuclet et al. |
| 2018/0369574 A1 | 12/2018 | Dubuclet et al. |
| 2019/0009052 A1 | 1/2019 | Oliverius et al. |
| 2019/0192826 A1 | 6/2019 | Wada |
| 2020/0138378 A1 | 5/2020 | de la Rama et al. |
| 2020/0253496 A1 | 8/2020 | Deno et al. |
| 2020/0405166 A1 | 12/2020 | Wu et al. |
| 2021/0145342 A1 | 5/2021 | Wang |
| 2021/0187246 A1 | 6/2021 | Houck |
| 2021/0204871 A1 | 7/2021 | Goedeke et al. |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0401345 A1 | 12/2021 | Wu et al. |
| 2022/0023594 A1 | 1/2022 | Pai |
| 2022/0054066 A1 | 2/2022 | Solis |
| 2022/0061727 A1 | 3/2022 | Olson et al. |

FOREIGN PATENT DOCUMENTS

| | | |
|---|---|---|
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 101927053 B | 1/2015 |
| CN | 103157168 B | 4/2015 |
| CN | 101797181 B | 12/2015 |
| CN | 105960201 B | 9/2016 |
| CN | 106264715 A | 1/2017 |
| CN | 106264716 A | 1/2017 |
| CN | 106308790 A | 1/2017 |
| CN | 106859765 A | 6/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 110536646 A | 12/2019 |
| CN | 111657866 A | 9/2020 |
| CN | 106264715 B | 11/2020 |
| CN | 106264716 B | 11/2020 |
| CN | 106308790 B | 6/2021 |
| CN | 107529958 B | 7/2021 |
| CN | 109310469 B | 7/2021 |
| CN | 109641121 B | 9/2021 |
| CN | 109952123 B | 9/2021 |
| CN | 110545874 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 108289709 B | 3/2022 |

(56) References Cited

FOREIGN PATENT DOCUMENTS

| | | | |
|---|---|---|---|
| EP | 0889744 | B1 | 1/2004 |
| EP | 1254641 | B1 | 11/2008 |
| EP | 1690564 | B1 | 4/2009 |
| EP | 1723981 | B1 | 8/2010 |
| EP | 2135634 | B1 | 10/2011 |
| EP | 2018203 | B1 | 6/2012 |
| EP | 1814450 | B1 | 1/2013 |
| EP | 2269532 | B1 | 3/2013 |
| EP | 2664295 | A1 | 11/2013 |
| EP | 2604306 | B1 | 1/2014 |
| EP | 2732843 | B1 | 5/2014 |
| EP | 2752153 | A1 | 7/2014 |
| EP | 2915555 | A1 | 9/2015 |
| EP | 1968679 | B1 | 9/2016 |
| EP | 2241279 | B1 | 9/2016 |
| EP | 3115076 | A4 | 10/2017 |
| EP | 3117863 | A4 | 10/2017 |
| EP | 3111871 | B1 | 3/2018 |
| EP | 3111872 | B1 | 4/2018 |
| EP | 3057488 | B1 | 5/2018 |
| EP | 2848226 | B1 | 7/2018 |
| EP | 3363397 | A1 | 8/2018 |
| EP | 2907462 | B1 | 9/2018 |
| EP | 3391928 | A1 | 10/2018 |
| EP | 3122276 | B1 | 11/2018 |
| EP | 3398549 | A1 | 11/2018 |
| EP | 1759668 | B1 | 12/2018 |
| EP | 3037122 | B1 | 12/2018 |
| EP | 2234537 | B1 | 1/2019 |
| EP | 2569040 | B1 | 2/2019 |
| EP | 3023052 | B1 | 3/2019 |
| EP | 3466363 | A1 | 4/2019 |
| EP | 2550989 | B1 | 6/2019 |
| EP | 3512589 | A1 | 7/2019 |
| EP | 3512590 | A1 | 7/2019 |
| EP | 3527125 | A1 | 8/2019 |
| EP | 3531903 | A1 | 9/2019 |
| EP | 3434218 | B1 | 2/2020 |
| EP | 2908723 | B1 | 3/2020 |
| EP | 3114987 | A1 | 8/2020 |
| EP | 3114987 | B1 | 8/2020 |
| EP | 3178516 | B1 | 9/2020 |
| EP | 3738508 | A1 | 11/2020 |
| EP | 3738509 | A1 | 11/2020 |
| EP | 3340916 | B1 | 12/2020 |
| EP | 3579908 | B1 | 12/2020 |
| EP | 3750475 | B1 | 12/2020 |
| EP | 2155301 | B1 | 4/2021 |
| EP | 3432820 | B1 | 4/2021 |
| EP | 3579758 | B1 | 5/2021 |
| EP | 2809254 | B1 | 6/2021 |
| EP | 3508245 | B1 | 7/2021 |
| EP | 3858277 | A1 | 8/2021 |
| EP | 3791820 | B9 | 4/2022 |
| IL | 246415 | A | 12/2019 |
| JP | 4545384 | B2 | 7/2010 |
| JP | 4887810 | B2 | 2/2012 |
| JP | 4940332 | B2 | 3/2012 |
| JP | 2012055602 | A | 3/2012 |
| JP | 2012200509 | A | 10/2012 |
| JP | 5154031 | B2 | 2/2013 |
| JP | 5193190 | B2 | 5/2013 |
| JP | 5372314 | B2 | 12/2013 |
| JP | 2014014713 | A | 1/2014 |
| JP | 5550150 | B2 | 5/2014 |
| JP | 5762697 | B2 | 6/2015 |
| JP | 5856712 | B2 | 2/2016 |
| JP | 5908270 | B2 | 4/2016 |
| JP | 5944331 | B2 | 7/2016 |
| JP | 6050522 | B2 | 12/2016 |
| JP | 2017012750 | A | 1/2017 |
| JP | 2017012755 | A | 1/2017 |
| JP | 2017038919 | A | 2/2017 |
| JP | 2017051211 | A | 3/2017 |
| JP | 2017104552 | A | 6/2017 |
| JP | 6246742 | B2 | 12/2017 |
| JP | 6342524 | B2 | 6/2018 |
| JP | 6434495 | B2 | 12/2018 |
| JP | 6445509 | B2 | 12/2018 |
| JP | 6445742 | B1 | 12/2018 |
| JP | 6466114 | B2 | 2/2019 |
| JP | 6515084 | B2 | 4/2019 |
| JP | 6528010 | B1 | 5/2019 |
| JP | 6655655 | B2 | 2/2020 |
| JP | 6776021 | B2 | 10/2020 |
| JP | 6776025 | B2 | 10/2020 |
| JP | 6786275 | B2 | 11/2020 |
| JP | 6821812 | B2 | 1/2021 |
| JP | 2021007772 | A | 1/2021 |
| JP | 6843502 | B2 | 3/2021 |
| JP | 6894004 | B2 | 6/2021 |
| JP | 6920312 | B2 | 8/2021 |
| JP | 6926306 | B2 | 8/2021 |
| JP | 6932484 | B2 | 8/2021 |
| JP | 6936872 | B2 | 9/2021 |
| JP | 6980386 | B2 | 11/2021 |
| JP | 2022020838 | A | 2/2022 |
| WO | 9843530 | A1 | 10/1998 |
| WO | 0168178 | A1 | 9/2001 |
| WO | 2008091197 | A1 | 7/2008 |
| WO | 2015057521 | A1 | 4/2015 |
| WO | 2015095577 | A1 | 6/2015 |
| WO | 2015130824 | A1 | 9/2015 |
| WO | 2016001015 | A1 | 1/2016 |
| WO | 2017070559 | A1 | 4/2017 |
| WO | 2017098198 | A1 | 6/2017 |
| WO | 2018053148 | | 3/2018 |
| WO | 2018053164 | | 3/2018 |
| WO | 2018136741 | | 7/2018 |

\* cited by examiner

MASKED RING ELECTRODES

CROSS REFERENCE TO RELATED APPLICATION

This application claims the benefit of U.S. Provisional Application Ser. No. 62/536,369, filed 24 Jul. 2017, the entire disclosure of which is incorporated by reference herein.

BACKGROUND a. Field

The present disclosure relates to electrophysiology catheters. In particular, the instant disclosure relates to an electrophysiology catheter having one or more partially insulated or masked electrodes that reduce or eliminate far field effects on electrical signals indicative of tissue in a region of interest.

b. Background

Electrophysiology (EP) mapping catheters are used to generate electrophysiology maps of tissue in a region of interest. The EP mapping data may be used, for example, in the diagnosis and treatment of tissues within a body. For example, EP maps of heart tissue can be used to guide ablation catheters which are used to convey an electrical stimulus to a region of interest within the heart and create tissue necrosis. Ablation catheters may be used to necrose heart tissue to correct conditions such as atrial and ventricular arrhythmias (including, but not limited to, ectopic atrial tachycardia, atrial fibrillation, atrial flutter and ventricular tachycardias). In addition to guiding ablation catheters, EP maps can also be used to evaluate the effectiveness of ablation therapy, or to locate ectopic sources or a critical isthmus.

An EP mapping catheter may include one or more electrodes at a distal end that samples electrical activity in tissue. Many EP mapping catheters have a relatively large number of electrodes to enable sampling over a relatively wide area of interest and reduce procedure time. Referring to FIG. 1, one type of EP mapping catheter 10 in use today includes a collapsible and expandable basket electrode assembly 12 disposed at the distal end of the catheter 10. The basket electrode assembly 12 assumes a compressed state as the catheter is maneuvered through an introducer sheath to a region of interest in the body and an expanded state once the catheter reaches the region of interest and emerges from the sheath. The basket electrode assembly 12 includes a plurality of splines 14 on which un-insulated or un-masked electrodes 16 are disposed. The splines 14 are coupled together at proximal and distal ends and bow outward (i.e. a bowed shape) when the basket assembly 12 is in an expanded state.

The foregoing discussion is intended only to illustrate the present field and should not be taken as a disavowal of claim scope.

BRIEF SUMMARY

The present disclosure relates to an electrophysiology catheter. In particular, the instant disclosure relates to an electrophysiology catheter having a plurality of partially-masked electrodes which, when placed in contact with the surface of a tissue of interest, the conductive material of the partially-masked electrode is not in contact with the blood pool.

A partially-masked electrode, in accordance with at least one embodiment of the present disclosure, includes a conductive material and an insulated coating having an outer surface. The insulated coating defines a contoured opening that exposes or reveals an area of the conductive material, wherein the contoured opening has an upper perimeter at the outer surface of the insulated coating. The upper perimeter of the opening defines an imaginary boundary area above the exposed area of the conductive material beyond which no part of the exposed conductive material extends.

A catheter in accordance with at least another embodiment of the present disclosure includes an elongate, deformable shaft comprising a proximal end and a distal end. The catheter further includes a distal tip assembly coupled to said distal end of said shaft, said distal tip assembly comprising a plurality of partially-masked electrodes disposed thereon. At least one of the plurality of partially-masked electrodes comprises a conductive material and an insulated coating having an outer surface. The insulated coating defines a contoured opening that exposes an area of the conductive material, wherein the contoured opening has an upper perimeter at the outer surface of the insulated coating. The upper perimeter of the opening defines an imaginary boundary area above the exposed area of the conductive material beyond which no part of the exposed conductive material extends.

A catheter in accordance with at least another embodiment of the present disclosure includes an elongate, deformable shaft having a proximal end and a distal end. The catheter further includes a distal tip assembly coupled to said distal end of said shaft, said distal tip assembly comprising a plurality of partially-masked electrodes disposed thereon. At least one of the plurality of partially-masked electrodes comprises a conductive material and an insulated coating having an outer surface, wherein the insulated coating defines a contoured opening that exposes or reveals an area of the conductive material. The contoured opening has an upper perimeter at the outer surface of the insulated coating. When the upper perimeter of the insulated coating is placed in contact with a tissue of interest, wherein the tissue of interest is proximate a blood pool, the insulated coating creates a seal between the blood pool and the contoured opening so that no blood in the blood pool can contact the conductive material.

A catheter in accordance with at least another embodiment of the present disclosure includes an elongate, deformable shaft having a proximal end and a distal end. The catheter further includes a basket electrode assembly coupled to the distal end of the shaft. The basket electrode assembly comprises a proximal end and a distal end, and is configured to assume a compressed state and an expanded state. The basket catheter assembly includes a first spline comprising a plurality of partially-masked electrodes disposed thereon. At least one of the plurality of partially-masked electrodes comprises a conductive material and an insulated coating having an outer surface, wherein the insulated coating defines a contoured opening that exposes or reveals an area of the conductive material. The contoured opening has an upper perimeter at the outer surface of the insulated coating. The upper perimeter of the opening defines an imaginary boundary area above the exposed area of the conductive material beyond which no part of the exposed conductive material extends.

A catheter in accordance with at least another embodiment of the present disclosure includes an elongate, deformable shaft comprising a proximal end and a distal end and a flexible tip portion located adjacent to the distal end of the shaft. The flexible tip portion comprises a flexible framework and a plurality of partially-masked electrodes disposed on the flexible framework and forms a flexible array of partially-masked electrodes adapted to conform to tissue. At least one of the plurality of partially-masked electrodes comprises a conductive material and an insulated coating having an outer surface, wherein the insulated coating defines a contoured opening that exposes or reveals an area of the conductive material. The contoured opening has an upper perimeter at the outer surface of the insulated coating. The upper perimeter of the opening defines an imaginary boundary area above the exposed area of the conductive material beyond which no part of the exposed conductive material extends.

A partially-masked electrode in accordance with at least another embodiment of the present disclosure includes a conductive material and an insulated coating having an outer surface. The insulated coating defines a contoured opening that exposes or reveals an area of the conductive material, wherein the contoured opening has an upper perimeter at the outer surface of the insulated coating. When the upper perimeter of the insulated coating is placed in contact with a tissue of interest, wherein the tissue of interest is proximate a blood pool, the insulated coating creates a seal between the blood pool and the contoured opening so that no blood in the blood pool can contact the conductive material.

A catheter in accordance with at least another embodiment of the present disclosure includes an elongate, deformable shaft having a proximal end and a distal end. The catheter further includes a basket electrode assembly coupled to the distal end of the shaft. The basket electrode assembly comprises a proximal end and a distal end and is configured to assume a compressed state and an expanded state and includes a first spline comprising a plurality of partially-masked electrodes disposed thereon. At least one of the plurality of partially-masked electrodes comprises a conductive material and an insulated coating having an outer surface, wherein the insulated coating defines a contoured opening that exposes or reveals an area of the conductive material. The contoured opening has an upper perimeter at the outer surface of the insulated coating. When the upper perimeter of the insulated coating is placed in contact with a tissue of interest, wherein the tissue of interest is proximate a blood pool, the insulated coating creates a seal between the blood pool and the contoured opening so that no blood in the blood pool can contact the conductive material.

A catheter in accordance with at least another embodiment of the present disclosure includes an elongate, deformable shaft comprising a proximal end and a distal end and a flexible tip portion located adjacent to the distal end of the shaft. The flexible tip portion comprises a flexible framework and a plurality of partially-masked electrodes disposed on the flexible framework and forming a flexible array of partially-masked electrodes adapted to conform to tissue. At least one of the plurality of partially-masked electrodes comprises a conductive material and an insulated coating having an outer surface, wherein the insulated coating defines a contoured opening that exposes or reveals an area of the conductive material. The contoured opening has an upper perimeter at the outer surface of the insulated coating. When the upper perimeter of the insulated coating is placed in contact with a tissue of interest, wherein the tissue of interest is proximate a blood pool, the insulated coating creates a seal between the blood pool and the contoured opening so that no blood in the blood pool can contact the conductive material.

A partially-masked electrode, in accordance with at least another embodiment of the present disclosure, includes an insulated coating that is selected and configured to allow the reception of a localization signal by a conductive material of the partially-masked electrode. The insulated coating is selected and configured to prevent the reception of at least a significant amount of a far field signal by the conductive material.

A catheter in accordance with at least another embodiment of the present disclosure includes an insulated coating on at least one partially-masked electrode that is selected and configured to allow the reception of a localization signal by a conductive material of the partially-masked electrode. The insulated coating on the at least one partially-masked electrodes configured to prevent the reception of at least a portion of a far field signal by the conductive material.

A partially-masked electrode in accordance with various embodiments of the present disclosure wherein the insulated coating is selected and configured to allow the reception of a localization signal by the conductive material; and wherein the insulated coating is configured to prevent the reception of at least a portion of a far field signal by the conductive material.

A catheter in accordance with various embodiments of the present disclosure, wherein the insulated coating of at least one of the partially-masked electrodes configured to receive a localization signal through the conductive material; and wherein the insulated coating of at least one of the partially-masked electrodes is configured to prevent the reception of at least a portion of a far field signal via the conductive material.

A method of using a catheter in accordance with various embodiments of the present disclosure, the method comprising tracking the location of at least one of the partially-masked electrodes within a body of a patient, wherein the insulated coating of at least one of the partially-masked electrodes is configured to receive a localization signal by the conductive material; and wherein the insulated coating of at least one of the partially-masked electrodes is configured to prevent the reception of at least a portion of a far field signal by the conductive material; and placing the upper perimeter of the insulated coating of at least one of the partially-masked electrodes in contact with a tissue of interest in the body of the patient, the tissue of interest being proximate a blood pool, such that the insulated coating creates a seal between the blood pool and the contoured opening to inhibit the receipt of the far field signal in the blood pool.

A method of using a catheter in accordance with various embodiments of the present disclosure, the method comprising: tracking the location of one of a plurality of partially-masked electrodes within a body of a patient; wherein the insulated coating of the partially-masked electrode is configured to receive a localization signal by the conductive material; and wherein the insulated coating of the partially-masked electrode is configured to prevent the reception of at least a portion of a far field signal by the conductive material; placing the upper perimeter of the insulated coating of the partially-masked electrode in contact with a tissue of interest at a first location in the body of the patient, the tissue of interest being proximate a blood pool, such that the insulated coating creates a seal between the blood pool and the contoured opening to inhibit the receipt of the far field signal in the blood pool; and receiving, via the partially-masked electrode, a first local electrical signal from the first location on the tissue of interest at the contoured opening, the first local electrical signal having a first magnitude, wherein as a result of the seal between the blood pool and the contoured opening the first local electrical signal comprises little or no far field signal.

The foregoing and other aspects, features, details, utilities, and advantages of the present disclosure will be apparent from reading the following description and claims, and from reviewing the accompanying drawings.

DETAILED DESCRIPTION

Figure 1:
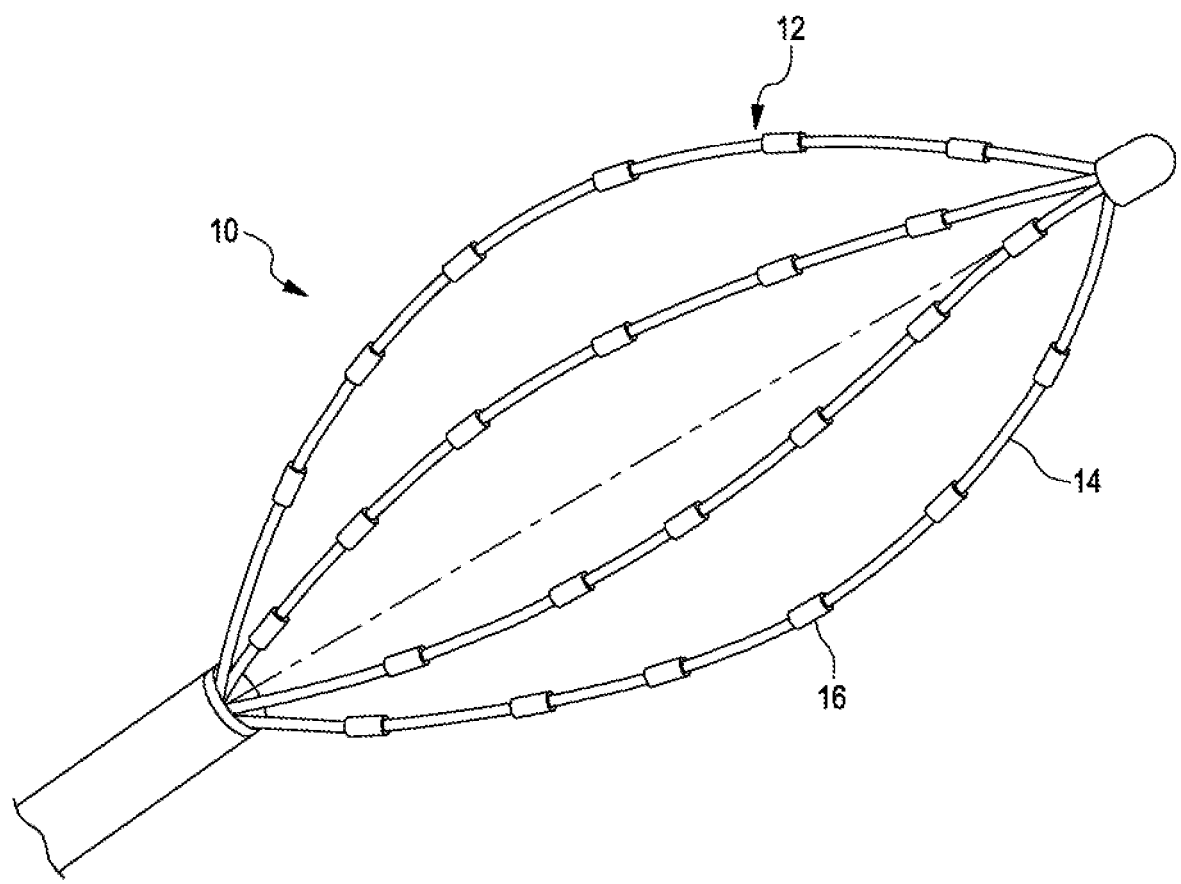
FIG. 1 is an isometric view of a prior art electrophysiology mapping catheter.

Typical catheter-based electrodes have predominantly been cylindrically-shaped (e.g., rings, tips, or spots). These electrodes have been used to take electrical signal measurements in a tissue of interest, for example the heart. As these electrodes are in the blood pool (or conductive pool), the electrodes will pick up various electrical signals in the heart, including signals proximal to the electrodes as well as signals distal the electrodes, the latter generally called far field effects. When an electrode is in contact with healthy tissue, a more distinct and/or stronger electrical signal is measured by the electrode. The electrical signal from the tissue is often referred to as a local source. However, in use, only a portion of a typical electrode, such as electrode 16 shown in FIG. 1, is in direct contact with the tissue of interest. Most of the electrode 16 is exposed to the blood pool and therefore the resulting output signal of the electrode 16 is a combination of local and far field effects. That is, the far field effects create noise in the received signal which makes it difficult to identify, locate, and/or diagnose unhealthy tissue.

Typically, the method to locate, identify, and/or diagnose unhealthy regions of tissue, such as diseased or damaged tissue (e.g., a lesion) includes sensing one or more electrophysiological characteristics from the tissue. However, the local electrical signals from unhealthy tissue are often much weaker than the local electrical signals from healthy tissue. In some instances, the magnitude of the local electrical signals from unhealthy tissue is about equal to or less than the far field magnitude. Therefore, it becomes difficult to distinguish between the far field and local effects. That is, the signal-to-noise ratio when sensing on or near unhealthy tissue may approach 1. The poor signal fidelity and/or low magnitude at the unhealthy tissue of interest makes it difficult to determine, for example, what is a boundary edge or conduction path/gap between unhealthy tissue and healthy tissue.

Additionally, as investigations and research in industry progress down the path of smaller electrode sizes and tighter physical positioning to increase the resolution for locating and identifying unhealthy tissue, aspects of the present disclosure are directed to the use of printed or flex circuit electrodes to increase resolution.

Some benefits of printed or flex circuit electrodes are that they can be manufactured via batch fabrication, which reduces costs, and allow for the design of small and/or close electrodes and associated electrical connections into a smaller space. In addition, the printed and/or flex circuit electrodes tend to be one-sided electrodes. That is, they are only conductive on one side, and thereby minimize exposure of the electrode to the blood pool enhancing signal fidelity. However, the focus of the industry so far has been on size and/or spacing optimization and not on tissue contact and/or far field isolation.

One disadvantage of printed or flex circuit-based electrodes and traces is the increase impedance to that of a typical ring electrode. Increased impedance is detrimental to impedance based location systems (e.g., higher signal-to-noise ratio), and may degrade the accuracy of sensed biosignals (ECG). These issues may also result in the increased noise from the printed or flex circuit electrodes as compared to typical ring electrodes, and may negate some of the isolation benefits of the one-sided structure of the printed or flex circuit electrode.

Additionally, printed or flex circuit electrodes tend to be planar and relatively smooth. Both of these qualities result in poor contact with tissue by the printed or flex circuit electrodes which may allow some blood pool contact and far field influence into a sensed electrophysiology signal.

In accordance with various embodiments of the present disclosure, catheters including electrodes which are partially-masked with an insulating material facilitate improved EP diagnostics. The insulating material of the partially-masked electrodes creates a seal between the blood pool and the conductive material of the partially-masked electrode which reduces or eliminates the reception of the far field effects by the partially-masked electrode, making it easier to locate and diagnose unhealthy tissue.

Figure 2:
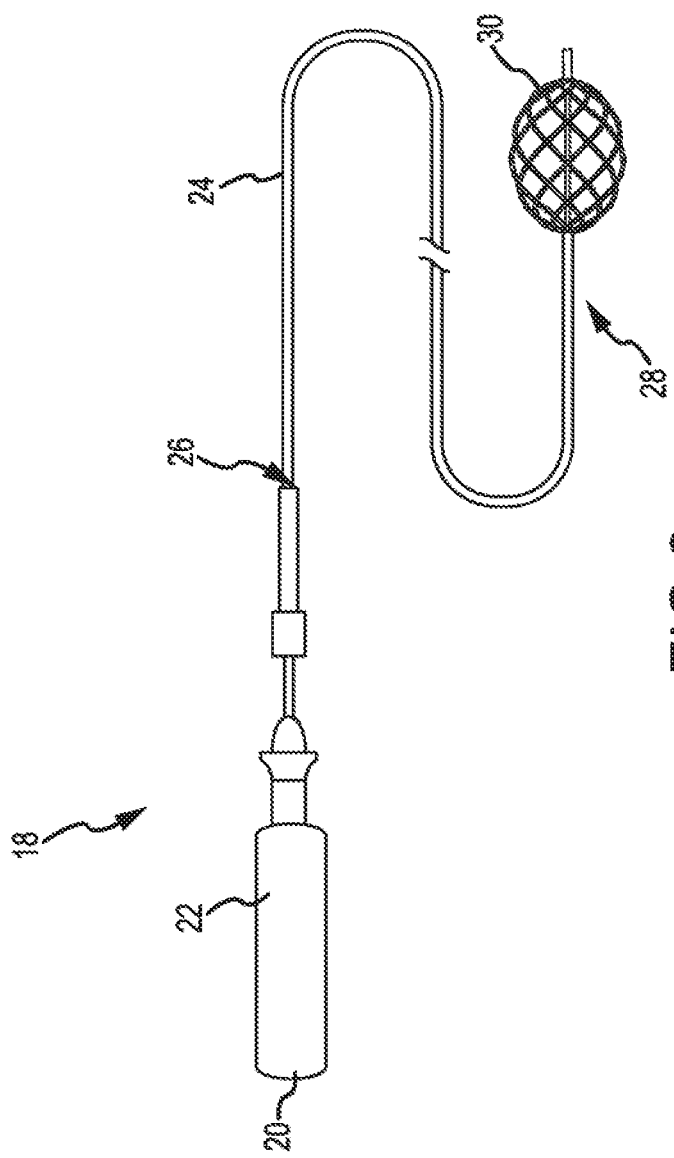
FIG. 2 is a diagrammatic view of an electrophysiology catheter according to an embodiment of the disclosure.

Referring now to the drawings wherein like reference numerals are used to identify identical components in the various views, FIG. 2 illustrates one embodiment of an electrophysiology catheter 18 having a plurality of partially-masked electrodes in accordance with the present disclosure. Catheter 18 is provided for use in generating an electrophysiological map of tissue and, in particular, cardiac tissue. It should be understood, however, that catheter 18 may be used in conjunction with various tissue types. Catheter 18 may include a cable connector or interface 20, a handle 22, a shaft 24 having a proximal end 26 and a distal end 28, and a distal tip assembly such as the basket electrode assembly 30 depicted in FIG. 2. Catheter 18 may also include other conventional components not illustrated herein such as deflection mechanisms, additional electrodes and corresponding conductors or leads.

Connector 20 provides mechanical and electrical connection(s) for cables extending from an electronic control unit (ECU) (not shown) or similar device that is configured to receive signals generated by basket electrode assembly 30. Connector 20 may be conventional in the art and be disposed at the proximal end 26 of catheter 18.

Handle 22 provides a location for the physician to hold catheter 18 and may further provides a means for steering or guiding shaft 24 within the body. For example, handle 22 may include means to change the length of a guide wire extending through catheter 18 to distal end 28 of shaft 24 to steer distal end 28 and, thus, shaft 24. Handle 22 may also be conventional in the art and it will be understood that the construction of handle 22 may vary.

Shaft 24 is an elongate, deformable member configured for movement within the body. Shaft 24 supports electrode assembly 30, associated conductors, and, in some embodiments, additional electronics used for signal processing or conditioning. Shaft 24 may also be configured to permit transport, delivery, and/or removal of fluids (including irrigation fluids and bodily fluids), medicines, and/or surgical tools or instruments. Shaft 24 may be made from conventional materials such as polyurethane and defines one or more lumens configured to house and/or transport electrical conductors, fluids, medicines, guide wires or surgical tools or instruments. Shaft 24 may be introduced into a blood vessel or other structure within the body through an introducer sheath. Shaft 24 may then be steered or guided through the body to a desired location such as tissue in a region of interest using guide wires or pull wires or other means known in the art including remote control guidance systems.

Figure 3:
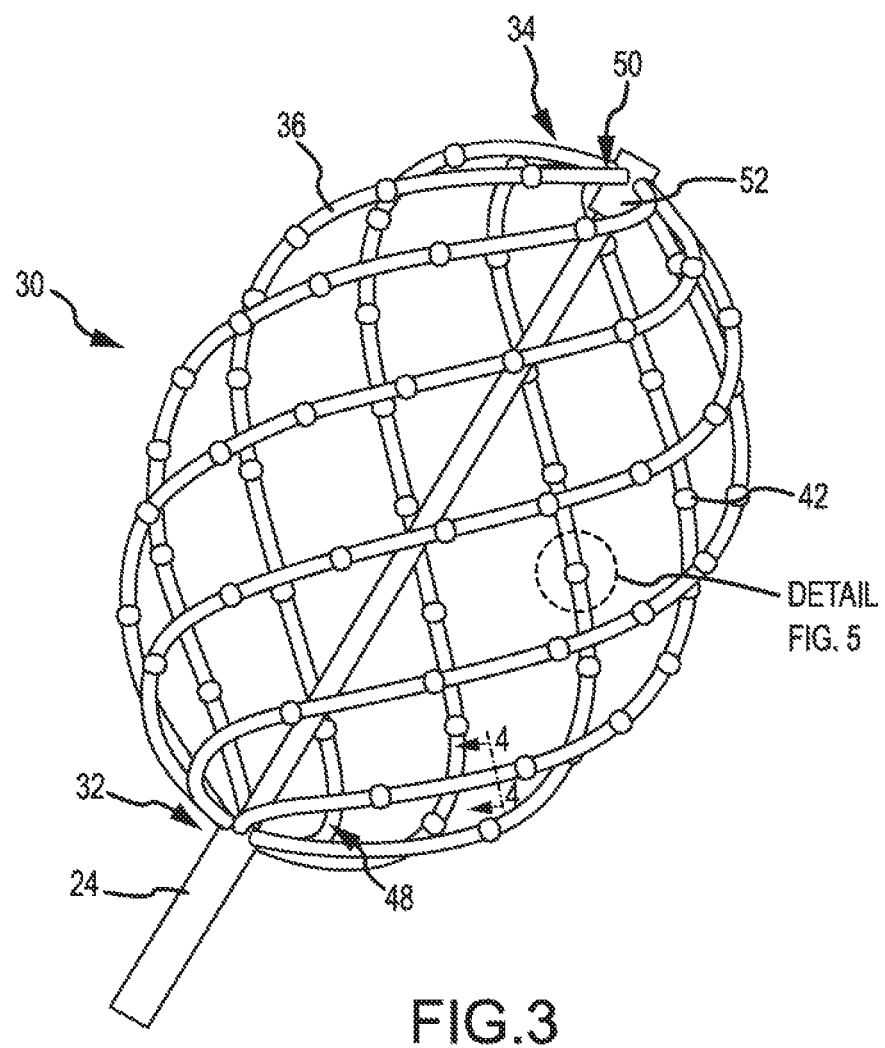
FIG. 3 is an enlarged isometric view of a distal tip assembly of the electrophysiology catheter of FIG. 2 comprising a basket electrode assembly.
Figure 4:
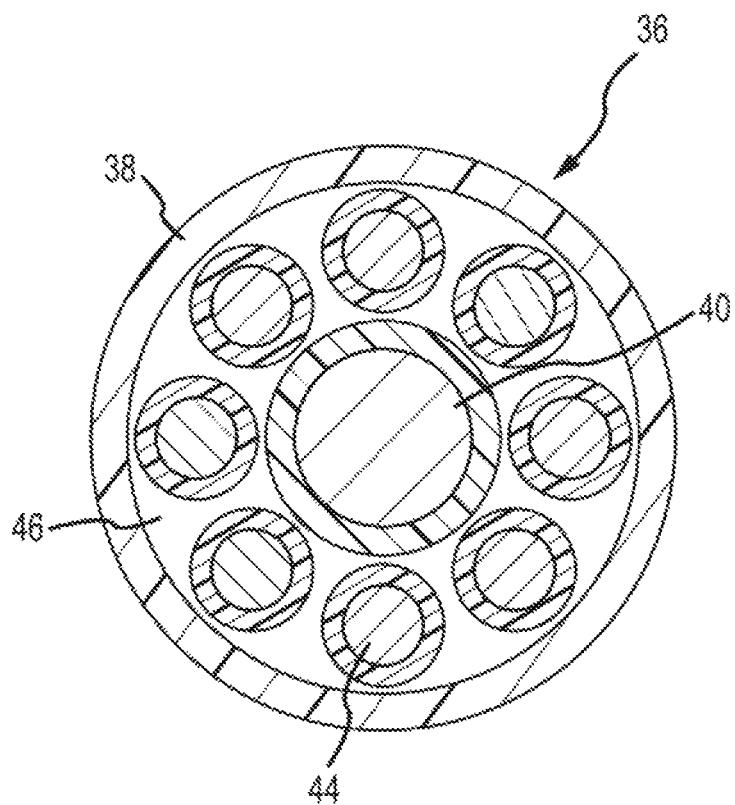
FIG. 4 is a cross-sectional view of a spline comprising part of the basket electrode assembly of FIG. 3, taken along line 4-4 in FIG. 3.
Figure 5:
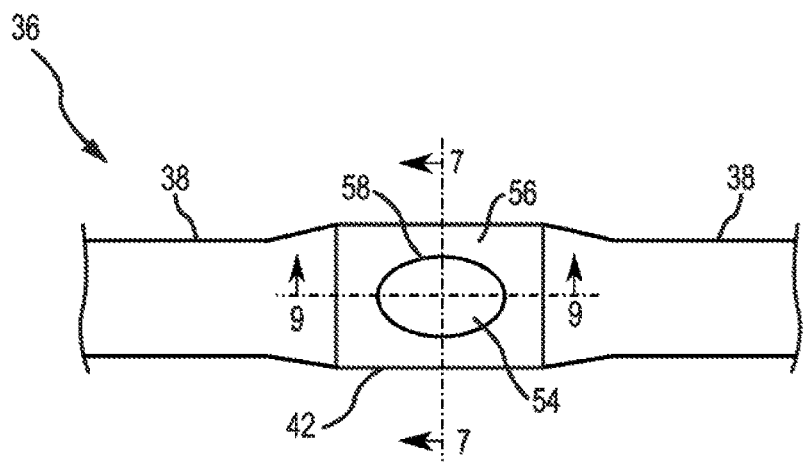
FIG. 5 is an enlarged side view of the region in the dashed circle labeled "FIG. 5" in FIG. 3, depicting a partially masked electrode on a section of a spline of the basket electrode assembly depicted in FIG. 3.

Referring now to FIGS. 3 and 4, basket electrode assembly 30 provides a means for conducting an electrophysiological study of tissue. Assembly 30 may be coupled to a distal end of shaft 24 and includes a proximal end 32 and a distal end 34. Assembly 30 may include a plurality of splines 36 on which electrodes are disposed and that form an electrode "basket" that is configured to assume a compressed state and an expanded state. Assembly 30 may assume the expanded state in the absence of an extraneous force acting on the assembly 30 (i.e., assembly 30 may be biased to the expanded state by, for example, nickel titanium memory alloy components) or may be urged to the expanded state through mechanical means (e.g., wires that are pulled or pushed) or by an internal balloon that can be expanded within the basket electrode assembly 30. Assembly 30 may assume the compressed state, for example, as catheter 18 is maneuvered through an introducer sheath within the body to the region of interest and assume the expanded state upon emerging from a distal end of the sheath. Splines 36 are configured to support electrodes in a predetermined configuration to allow contact and/or non-contact mapping of electrical activity in tissue. Referring to FIG. 4, each spline 36 may include a tubular body 38, means, such as wire 40, for supporting (and biasing) body 38 to assume a predetermined shape, one or more partially-masked electrodes 42 (as shown in FIG. 3), and associated conductors 44. Although a particular embodiment for a spline, e.g., spline 36, is illustrated herein, it should be understood that spline(s) may be constructed in a variety of ways. In one embodiment, for example, one or more splines may include a flexible circuit as described and illustrated in U.S. patent application Ser. No. 12/958,992 (published as United States Patent Application Publication no. 2012/0143298 A1), the entire disclosure of which is incorporated by reference as though fully set forth herein. Additional embodiments of splines and/or basket electrode assemblies may be found described in one or more of U.S. patent application Ser. No. 13/072,357 (published as United States Patent Application Publication No. US 2011/0213231 A1) and U.S. patent application Ser. No. 13/340,760 (published as United States Patent Application Publication No. US 2013/0172715), the entire disclosures of which are incorporated by reference as though fully set forth herein.

Body 38 provides structural support for partially-masked electrodes 42 and insulates conductors 44 from bodily fluids and other elements. Referring to FIG. 4, body 38 is tubular and may be annular in shape. It should be understood, however, that the shape of body 38 may vary. Body 38 may be made from conventional polymeric materials such as polyurethane, and nylon or thermoplastic elastomers such as the elastomer sold under the registered trademark "PEBAX" by Arkema, Inc. and reinforcements such as metallic braids. Body 38 may define a central lumen 46 extending between proximal and distal ends 48, 50 (as shown in FIG. 3) of body 38 and configured to allow passage of wire 40 and conductors 44. It should be understood, however, that body 38 may alternatively define one or more channels each configured to receive one of wire 40 or a conductor 44. In the illustrated embodiment, wire 40 is illustrated at the center of lumen 46 with conductors 44 disposed circumferentially around wire 40. It should be understood, however, that the relative arrangement of wire 40 and conductors 44 within lumen 46 may vary.

Wire 40 is provided to support and bias body 38 to assume a predetermined shape. Wire may be made from a shape memory alloy such as nitinol (nickel titanium). Wire extends through lumen 46 of body 38 from proximal end 48 of body 38 to distal end 50 and may extend through the bodies 38 of multiple splines 36 to couple one or more splines together. Alternatively, or in addition, splines 36 may be coupled at distal end 50 by a hinge connector 52 or in any of the ways described and illustrated in U.S. patent application Ser. No. 13/340,760 (published as United States Patent Application Publication No. US 2013/0172715), the entire disclosure of which is incorporated by reference as though fully set forth herein. The distal end 34 of the basket electrode assembly 30 may be specialized to form a small, but blunt mechanical connection point so that the distal portion of the catheter 18 may safely be pressed against tissue.

Referring again to FIG. 3, partially-masked electrodes 42 may be configured to diagnose, sense, and measure electrical activity in tissue such as cardiac tissue. One or more partially-masked electrodes 42 may also be used to provide tissue ablation therapy. Each partially-masked electrode 42 is coupled to a corresponding conductor 44 or one or more electrodes being coupled to the same conductor with the signal being multi-plexed.

Referring again to FIGS. 3 and 4, conductors 44 may be configured to transmit electrical signals from partially-masked electrodes 42 through shaft 24 of catheter 18 to an electronic control unit or similar device. Conductors 44 may comprise wires or cables or other means for conducting signals and may be disposed with the lumen 46 of a body 38 of a given spline 36. Each conductor 44 may be coupled at a distal end to a corresponding partially-masked electrode 42 and extend through lumen 46 to the proximal end 32 of basket electrode assembly 30.

Referring now to FIGS. 5-9, each of the partially-masked electrodes 42 may be formed of a conductive band 54 attached circumferentially about body 38. For the purposes of clarity, the internals of body 38 shown in FIG. 4 are not represented in FIGS. 7, 8, and 9. The conductive bands 54 may be composed of platinum, gold, stainless steel, iridium, or alloys of these metals, or other biocompatible, electrically-conductive materials or compositions thereof. The conductive bands 54 of each partially-masked ring electrode 42 may have an electrically-insulating, polymer surface coating 56. The surface coating 56 may be formed of a material with high dielectric properties that can be applied in a very thin layer. Exemplary surface coatings may include thin coatings of polyester, polyamides, polyimides, and blends of polyurethane and polyimides. In one embodiment, for example only and without limitation, surface coating 56 may be Parylene (e.g., Parylene C, Parylene N). In other embodiments, for example only and without limitation, surface coating 56 may be an acrylated urethane. In various embodiments, for example only and without limitation, the thickness of the surface coating 56 may range from about 0.0001 mm to about 0.05 mm. In other embodiments, for example only and without limitation, the thickness of the surface coating 56 may range from about 0.0003 mm to about 0.0006 mm. In various embodiments, for example only and without limitation, the surface coating 56 may be thicker around the opening 58 in order to create a taller "wall" to aid in creating a seal between the conductive band 54 and the blood pool, and thinner around the rest of the conductive band 54 to aid in reception of the localization signal by the partially-masked electrode 42.

An aperture is formed in the insulated surface coating 56 to create a contoured opening 58 that exposes or reveals a small area of the conductive band 54. The contoured opening 58 may be formed by laser, chemical, or other material removing or etching process to remove a portion of the insulated surface coating 56 to expose the conductive band 54 underneath. The edges or corners of the contoured opening 58 may be curved, rounded, or otherwise contoured to minimize any edge effects that could arise due to the imposition of a sharp edge, corner, or point. In various embodiments, for example only and without limitation, the openings 58 are oriented on the partially-masked electrodes 42 such that when the splines 36 of basket electrode assembly 30 are expanded, the openings 58 are facing the tissue of interest, such that they can contact the tissue of interest. In other embodiments, for example only and without limitation, the openings 58 are oriented on the partially-masked electrodes 42 such that when the splines 36 of basket electrode assembly 30 are expanded, the openings 58 may be maneuvered or oriented such that they are facing the tissue of interest and can contact the tissue of interest.

Although the contoured opening 58 is shown as having an oval shape, it will be understood that opening 58 may have other shapes, with or without rounded edges or corners, without departing from the scope of the disclosure, including, for example only and without limitation, a circle, an ellipse, a diamond, a rectangle, a hexagon, a square, a pentagon, an irregular polygon, a triangle. Opening 58 may be of different sizes without departing from the scope of the disclosure. For example only and without limitation, where opening 58 is a circle, the diameter of the opening 58 may range from about 0.010 mm to about 0.050 mm. In one embodiment, for example only and without limitation, the diameter of the opening 58 may be about 0.014 mm. In another embodiment, for example only and without limitation, the diameter of the opening 58 may be about 0.022 mm. In yet another embodiment, for example only and without limitation, the diameter of the opening 58 may be about 0.031 mm. Moreover, although a single opening 58 is shown per partially-masked electrode 42, it will be understood that each partially-masked electrode 42 may include more than one opening 58 (e.g., 2, 3, 4, or more) without departing from the scope of the disclosure.

In some embodiments, for example only and without limitation, the surface area of the conductive band 54 exposed at the opening 58 is only about 10 percent (10%) of the total surface area of the conductive band 54. Stated another way, about 90 percent (90%) of the conductive band 54 is insulated. Therefore, the electrically-conductive surface area of electrode 42 is only about 10 percent (10%) of the electrically-conductive surface area of a typical un-masked (un-insulated) ring electrode. In various embodiments, for example only and without limitation, the surface area of an un-insulated ring electrode may be about 2.5 mm$^2$ whereas the surface area of the opening 58 and thus the exposed area of conductive band 54 is about 0.25 mm². In various embodiments, for example only and without limitation, the exposed area of conductive band 54 may be from about 0.01 mm² to about 1.0 mm². In other embodiments, for example only and without limitation, the exposed area of conductive band 54 may be from about 0.044 mm² to about 0.486 mm².

Figure 6:
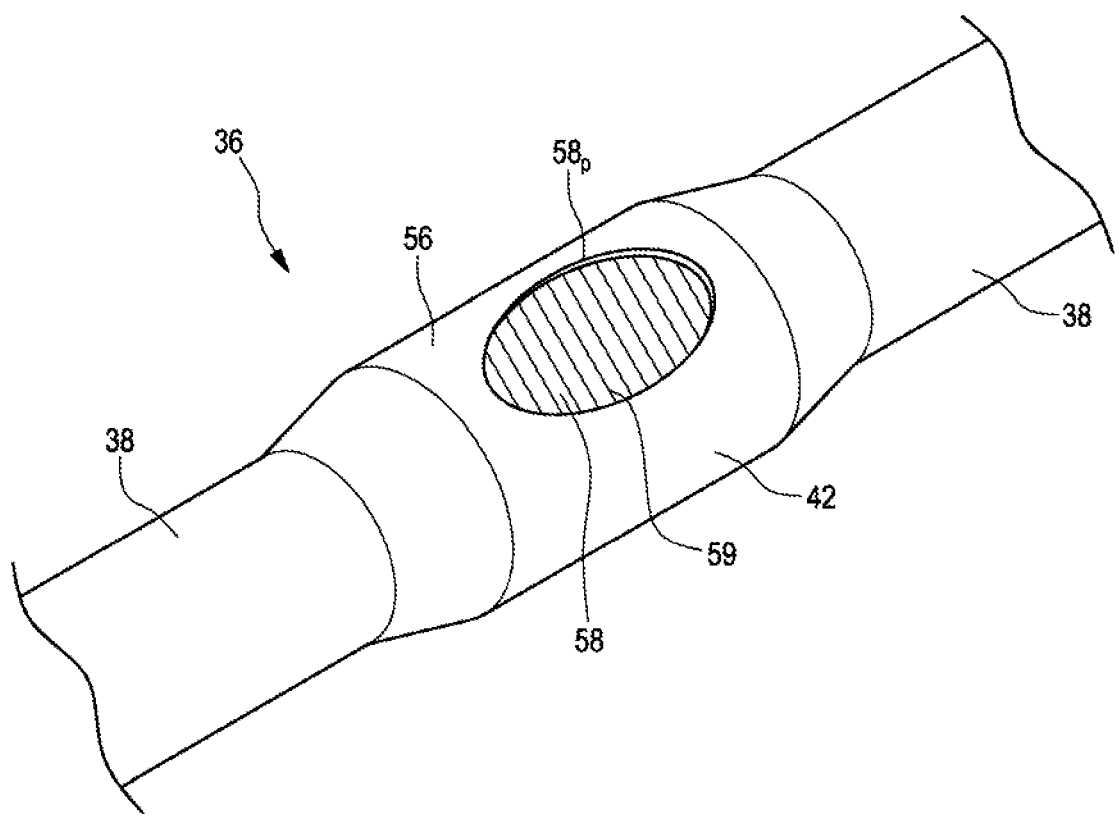
FIG. 6 is an enlarged isometric view of the region in dashed circle 5 in FIG. 3.
Figure 7:
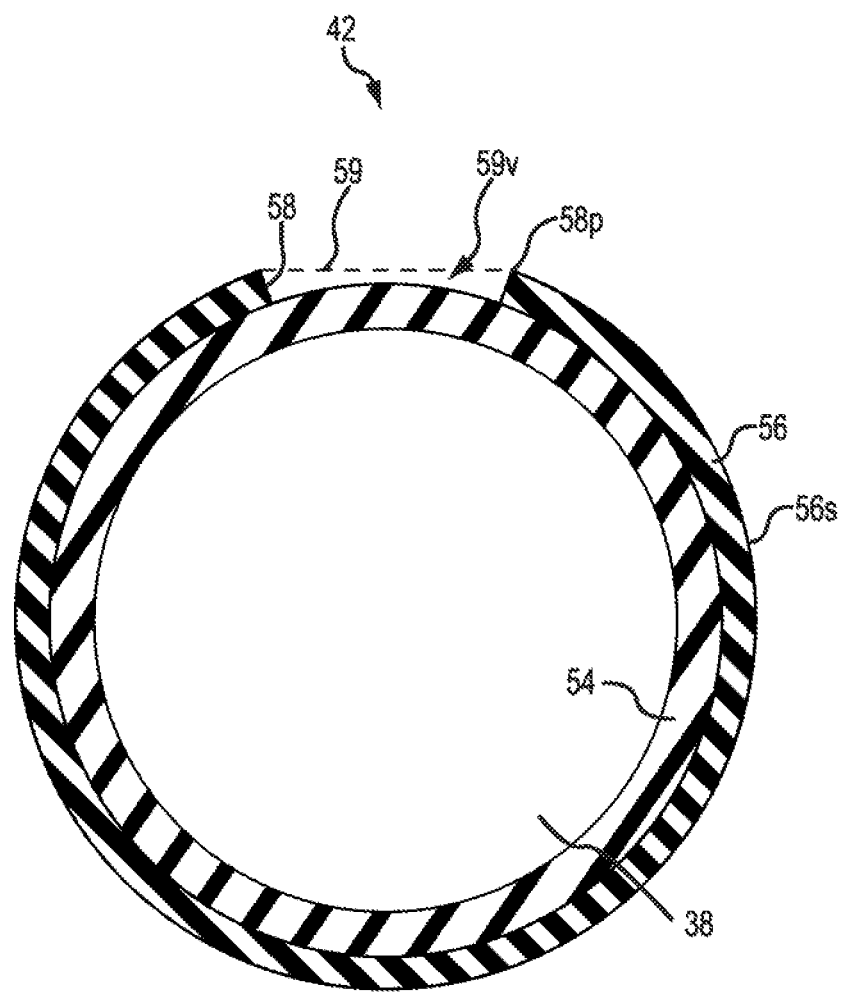
FIG. 7 is an enlarged, cross-sectional view of the partially-masked electrode depicted in FIGS. 5 and 6, taken along line 7-7 of FIG. 5.

As shown in FIGS. 6 and 7, opening 58 has an upper perimeter 58p at the outer surface 56s of the surface coating 56. The upper perimeter 58p of opening 58 defines an imaginary boundary area 59 above the exposed area of the conductive band 54 beyond which no part of the exposed conductive band 54 extends. The imaginary boundary area 59 is an imaginary surface having an outer edge(s) which is/are coincident and coextensive with the upper perimeter 58p of opening 58. Depending on the shape of opening 58, the imaginary boundary area 59 may be a plane or may have a contoured surface such as, for example only and without limitation, a saddle shape, a hyperbolic paraboloid, and a parabolic cylinder. The imaginary boundary area 59 is represented in FIG. 6 by a series of lines covering opening 58 within upper perimeter 58p. The imaginary boundary area 59 is represented in FIG. 7 by a dashed line extending from one side of the opening 58 to the other side of the opening within upper perimeter 58p. Therefore partially-masked electrode 42 includes a gap or void 59v between imaginary boundary area 59 and conductive band 54.

Figure 8:
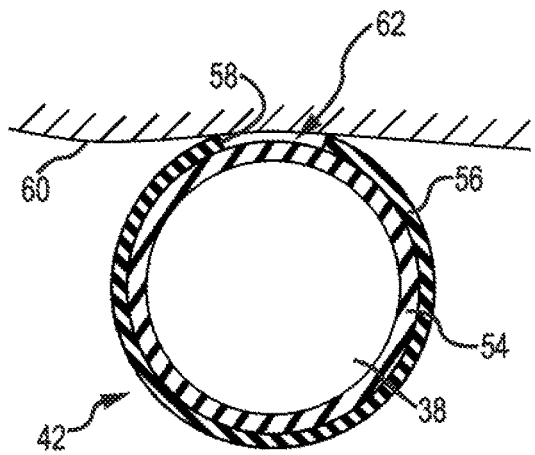
FIG. 8 is a cross-sectional side view of a partially-masked electrode positioned against a tissue of interest.
Figure 9:
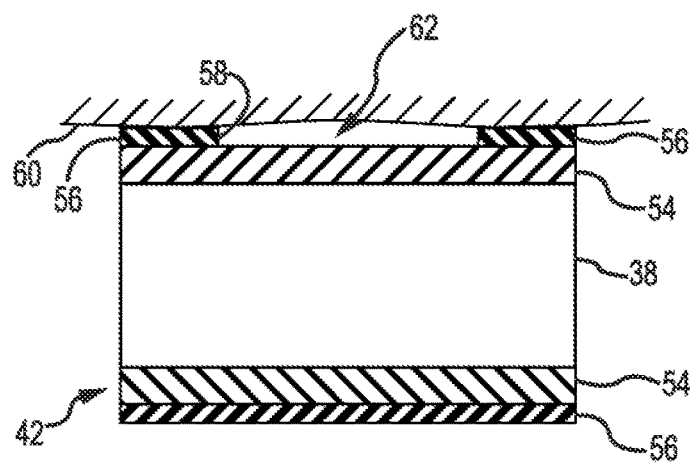
FIG. 9 is a cross-sectional view taken along line 9-9 of FIG. 5, with the partially-masked electrode positioned against a tissue of interest.

Referring now to FIGS. 8 and 9, partially-masked electrode 42 is shown interfacing with the surface 60 of a tissue of interest. As shown in the end view of FIG. 8 and the side view of FIG. 9, the surface coating 56 is between the conductive band 54 and the surface 60 of the tissue of interest. Because no part of conductive band 54 extends beyond the imaginary boundary area 59 shown in FIGS. 6 and 7, a void 62 is created between the conductive band 54 and the surface 60 of the tissue of interest at the location of the opening 58 in the surface coating 56. It is desirable to have the void 62 be as small as possible to increase the signal received by the partially-masked electrode 42. Thus, if the surface 60 of the tissue is touching the conductive band 54 the received signal may be increased.

Even if the surface 60 of the tissue does not come into contact with the conductive band 54, the raised surface coating 56 which is between the conductive band 54 and the surface 60, the thickness of the surface coating 56 creates a cupped or cup-like profile at the opening 58 which isolates the conductive band 54 of the partially-masked electrode 42 from the conductive path through the blood pool. That is, when the upper perimeter 58p of the raised surface coating 56 is placed in contact with the surface 60 of the tissue of interest, the surface coating 56 creates a seal between the blood pool and the opening 58 so that no blood in the blood pool can contact conductive band 54. When the opening 58 is oriented toward the tissue of interest and the surface coating 56 around the perimeter of the opening 58 makes contact with the surface 60 of the tissue of interest, the conductive band 54 is completely isolated or sealed from any far field effects present in the blood pool. This will be even more effective in smoother tissue than in rougher tissue. With typical unmasked electrodes, due to the combination of the rough surface and far field interference, the signal received by a typical unmasked electrode may be inaccurate. However, with a partially-masked electrode 42, even if a complete seal may not be able to be achieved against rough ventricle surface, for example. The isolation provided by the surface coating 56 of the partially-masked electrode 42 (with potentially more sealing at a tissue peak than a tissue valley) will still provide net improvement in EP measurements, as compared to a typical un-masked electrode. Except for opening 58, partially-masked electrode 42 has no other open conductive ends or portions as with typical ring electrodes. This results in a more focused electrode as compared to un-masked electrodes. Thus it is desirable to minimize the volume of the void 62 while maintaining the seal from the blood pool provided by surface coating 56.

Figure 10A:
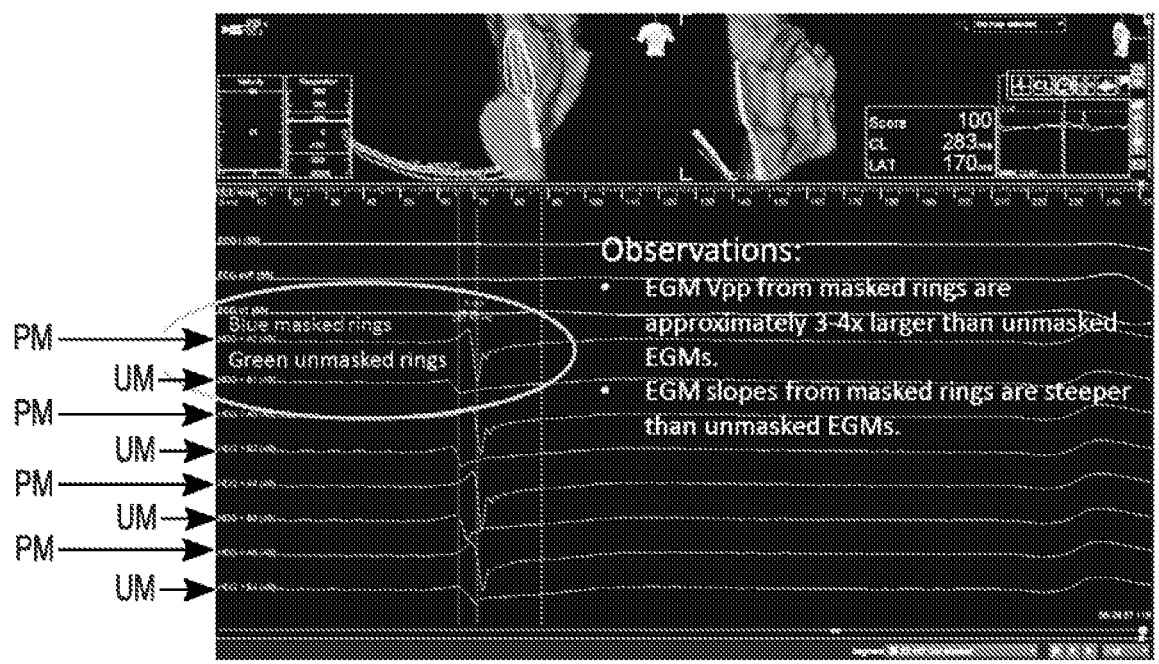
FIG. 10A is a graphical user interface display showing measured electrocardiogram voltages of a prior art unmasked electrode and a partially-masked electrode, according to various embodiment of the disclosure.

By completely isolating partially-masked electrode 42 from any far field effects present in the blood pool, the noise from the far field effects is significantly reduced or eliminated. This increases the signal to noise ratio of the electrical signal measured by the partially-masked electrode 42. Because the far field effects are no longer measured by the partially-masked electrode 42, the signal quality and magnitude of the measured weak local electrical signals from unhealthy tissue is improved as compared to a typical un-insulated ring electrode 16. This also allows for easier identification, locating, detecting and/or diagnosing unhealthy tissue. For example, as shown in FIG. 10A, pre-clinical testing has shown that the electrogram (EGM) peak-to-peak voltage (Vpp) signal from partially-masked electrode 42 (identified by arrows labeled PM) is about three to four times the magnitude of a typical un-insulated ring electrode 16 (identified by arrows labeled UM). In one embodiment, the measured peak-to-peak voltage (Vpp) signal from partially-masked electrode 42 was about 13.5 mV compared to 3.5 mV from a typical un-insulated ring electrode 16. Additionally, the slopes of the EGM signals from partially-masked electrode 42 were steeper than those measured by a typical un-insulated ring electrode 16.

In various embodiments, the surface coating 56 material and/or the surface coating 56 thickness is selected and configured to inhibit or block the receipt of the far field electrical signals when the surface coating 56 creates a seal between the blood pool and the opening 58, while still allowing the partially-masked ring electrode 42 to receive a localization signal. That is, the surface coating 56 is of a sufficient thickness and has material properties or characteristics such that the far field electrical signals cannot penetrate the surface coating 56 to the underlying conductive band 54, but still allows the localization signal to penetrate the surface coating 56 to the underlying conductive band 54. Thus, partially-masked electrode 42 can function as both an electrode for mapping and/or diagnostic purposes and for localization purposes. In essence, the surface coating 56 substantially or completely filters out the far field signals, with minimal or no filtering out of the localization signals. For example, through the selection and configuration of the material and/or thickness of the surface coating 56, the partially-masked electrode 42 may be tuned to filter out far field signals from about 1.0 Hz to about 600 Hz while being receptive to localization signals at or above approximately 8 kHz. Thus, the partially masked electrode 42 can filter out frequencies around the normal heart rate frequency (i.e., 1.0 Hz to about 1.67 Hz. The insulating properties of the insulated surface coating 56 therefore, may be frequency dependent.

Figure 10B:
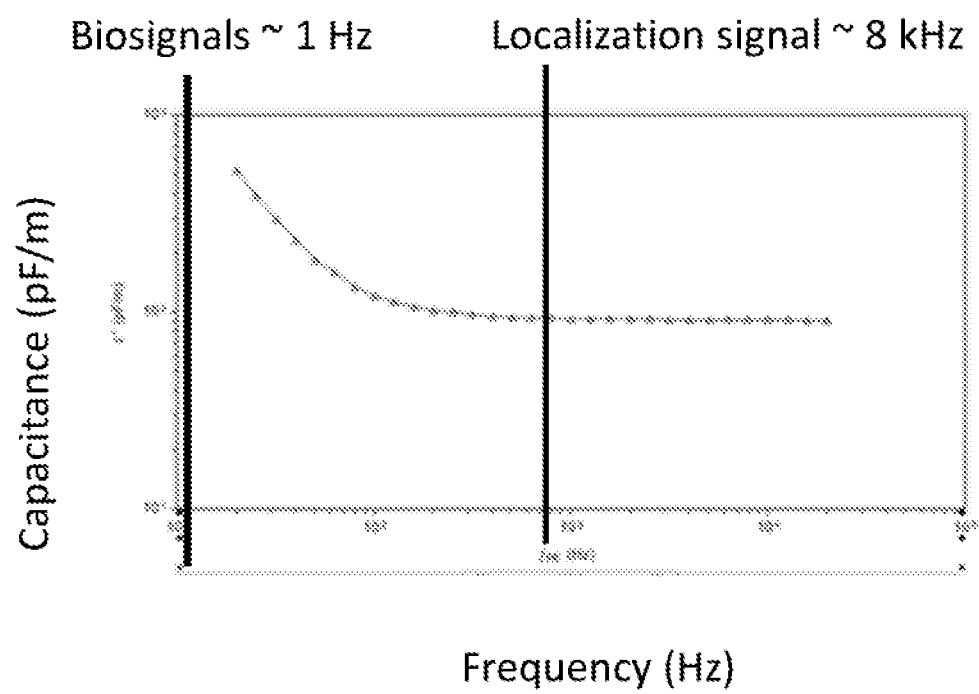
FIG. 10B is a graph showing the measured capacitance frequency response of an acrylated urethane masking material, according to an embodiment of the disclosure.
Figure 10C:
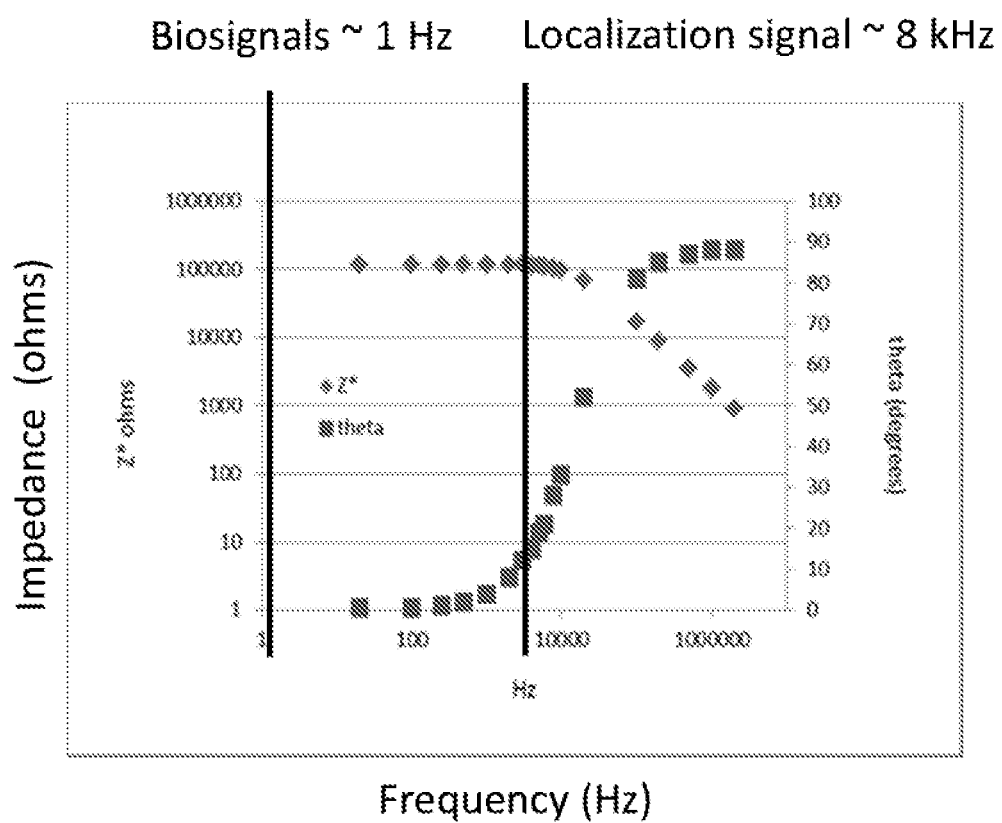
FIG. 10C is a graph showing the measured impedance of an acrylated urethane masking material, according to an embodiment of the disclosure.

FIGS. 10B and 10C illustrate frequency response and impedance of an acrylated urethane insulated surface coating having a thickness of 0.5 mm. It is believed that the measured properties of the acrylated urethane insulated surface coating will behave similarly when applied to conductive band 54 to create an embodiment of partially-masked electrode 42. For example, as shown in FIG. 10B, the capacitance is much higher at lower frequencies (e.g., from about 1.0 Hz to about 300 Hz), and decreases before substantially leveling off at higher frequencies (e.g., from about 400 Hz and above). It is expected that a partially-masked electrode 42, that is partially-masked with an acrylated urethane insulated surface coating having a thickness of 0.5 mm, will effectively filter out lower frequency signals (including far field biosignals), but will not filter out higher frequency signals (including localization signals). For example only and without limitation, the localization signal may be a current pulse as described in U.S. Pat. No. 7,263,397, the entire disclosure of which is incorporated by reference as though fully set forth herein. Thus it is expected that the partially-masked electrode 42 will work like a high-pass filter, and will have an equivalent circuit like a parallel RC (resistor-capacitor) circuit. The capacitance change shown in FIG. 10B results in the impedance curves shown in FIG. 10C. The increase in capacitance, at low frequency, will effectively act as a far-field biosignal filter by dielectric relaxational screening of the non-contact low frequency noise.

As shown in FIG. 10C, a resultant real component impedance of a tested acrylated urethane insulated surface coating with a thickness of 0.5 mm is equal to ($z^*\cos(\theta)$). Thus it is expected that a partially-masked electrode 42 having a 0.5 mm thick acrylated urethane insulated surface coating 56 will result in an impedance of about 90 k ohms between 100 Hz and 10 kHz. Accordingly, an insulated surface coating 56 of 5 µm will have an impedance of about 900 ohms. This impedance is within the range measured between partially-masked and unmasked electrodes. Therefore, the increased impedance of the partially-masked electrodes is still usable with impedance-based localization systems, such that the partially-masked electrodes 42 may be used for localization purposes as well as measuring biosignals from tissues of interest.

Pre-clinical testing has also shown that partially-masked electrodes, where the surface area of the opening 58 is only about 10 percent (10%) of the total surface area of the conductive band 54, had a smaller impedance increase than printed or flex circuit electrodes. Thus the impedance localization performance impact is minimized as compared to printed or flex circuit electrodes. The impedance of the partially-masked electrodes only increases from about 200-350 ohms to a range of about 430-610 ohms, as compared to unmasked electrodes.

Although partially-masked electrodes 42 are incorporated into a basket catheter having the structure shown in FIGS. 2 and 3, it will be understood that partially-masked electrodes 42 may be used in any type of catheter structure without departing from the scope of the disclosure. For example only and without limitation, partially-masked electrodes 42 may be incorporated into any of the basket catheter structures as described and illustrated in U.S. patent application Ser. No. 15/333,798 (published as U.S. Patent Application Pub. No. 2017/0100075), U.S. patent application Ser. No. 15/155,277 (published as U.S. Patent Application Pub. No. 2016/0331254), U.S. Pat. Nos. 9,339,331, and 8,224,416, the entire disclosures of which are incorporated by reference as though fully set forth herein.

Figure 11:
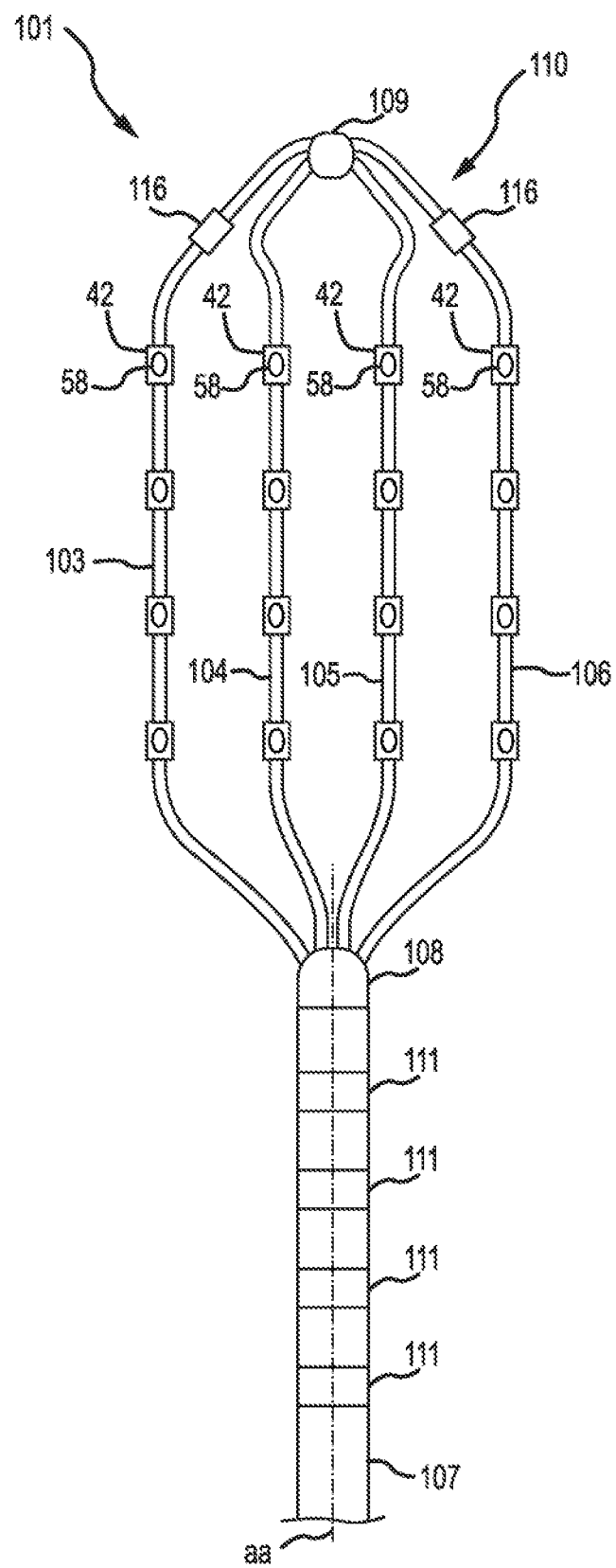
FIG. 11 is a top plan view of a distal tip assembly comprising a planar array of partially-masked electrodes, according to another embodiment of the disclosure.
Figure 12:
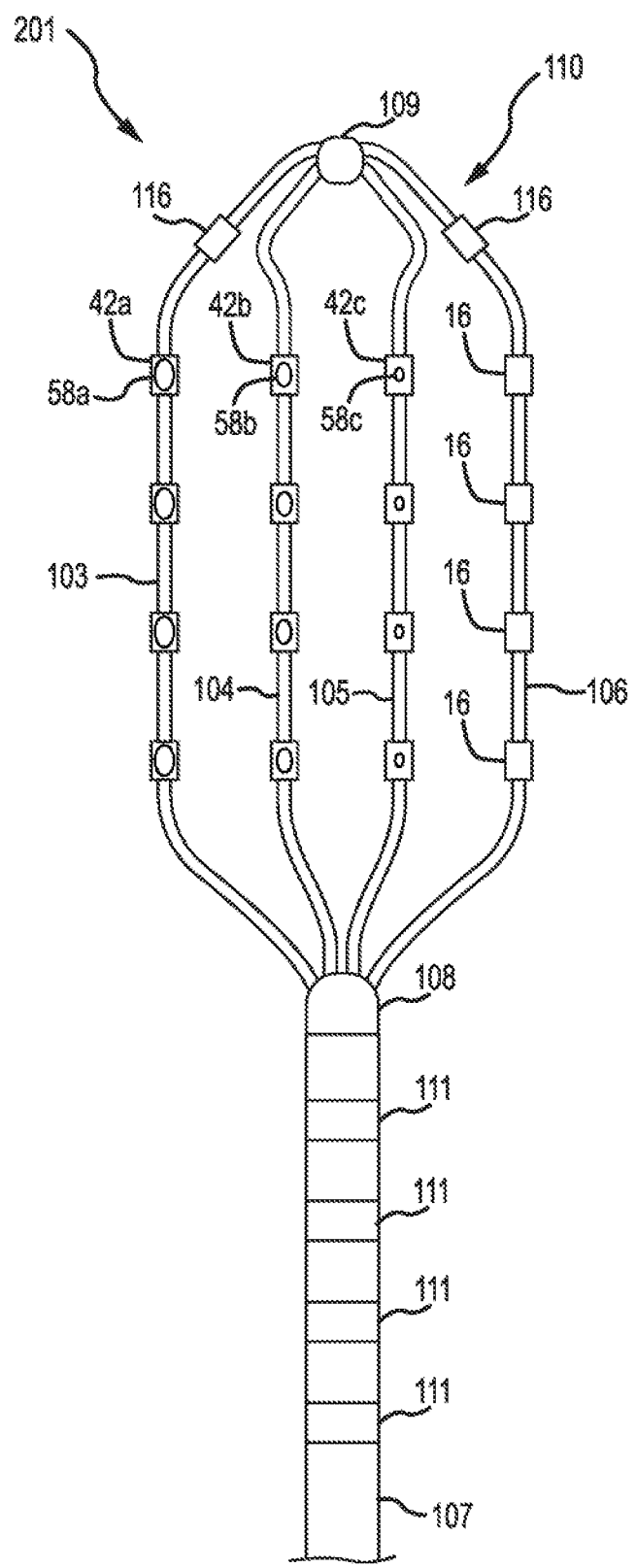
FIG. 12 is a top plan view of a distal tip assembly comprising a planar array of partially-masked electrodes, according to another embodiment of the disclosure.

In addition to being incorporated into basket catheter structures, partially-masked electrodes 42 may be incorporated into another distal tip assembly comprising a planar array of partially-masked electrodes. The distal tip assembly may be, for example, a high density electrode assembly as shown in FIGS. 11 and 12. FIG. 11 depicts a top view of a high density electrode assembly 101 according to various embodiments of the present disclosure. In some embodiments, the high density electrode assembly 101 may include a flexible tip portion 110 that forms a flexible array of partially-masked electrodes 42 having openings 58 in an insulated coating. This planar array (or 'paddle' configuration) of partially-masked electrodes 42 comprises four side-by-side, longitudinally-extending arms 103, 104, 105, 106, which can form a flexible framework on which the partially-masked electrodes 42 are disposed. The four microelectrode-carrier arms comprise a first outboard arm 103, a second outboard arm 106, a first inboard arm 104, and a second inboard arm 105. These arms are laterally separated from each other. In some embodiments, as shown in FIG. 11, there may be a distal member (or 'button') 109 where one or more of the arms come together. This distal member 109 may be constructed from metal or some other radiopaque material to provide fluoro visualization and semi-independent planar movement between the outer and inner arms. In other embodiments, high density electrode assembly 101 does not include distal member 109. In various embodiments, for example only and without limitation, high density electrode assembly 101 may be used for electrophysiology (EP) mapping. In other embodiments, for example only and without limitation, high density electrode assembly 101 may be used for tissue ablation.

Each of the four arms may carry a plurality of partially-masked electrodes 42. For example, each of the four arms can carry partially-masked electrodes 42 spaced along a length of each of the four arms. Although the high density electrode assembly 101 depicted in FIG. 11 depicts four arms, the high density electrode assembly 101 could comprise more or fewer arms. As shown in FIG. 11, one or more of the arms may include electrode 116, which may be an un-masked, partially-masked, or fully masked electrode. In some embodiments, for example only and without limitation, electrodes 116 may be fully masked and may be used for localization purposes. For example, as described in greater detail above, electrodes 116 may be masked with an insulated coating that isolates the conductive material of electrode 116 from far field or tissue signals (e.g., cardiac signals), but does not isolate electrode 116 from localization signals. Additionally, while the high density electrode assembly 101 depicted in FIG. 11 depicts 16 partially-masked electrodes (e.g., 4 partially-masked electrodes 42 on first outboard arm 103 and second outboard arm 106 and 4 partially-masked electrodes 42 on first inboard arm 104 and second inboard arm 105), the catheters can include more or fewer than 16 partially-masked electrodes. In addition, the first outboard arm 103 and second outboard arm 106 can include more or fewer than 4 partially-masked electrodes and the first inboard arm 104 and second inboard arm 105 can include more or fewer than 4 partially-masked electrodes.

While the partially-masked electrodes are shown as substantially equally distributed on arms 103, 104, 105 and 106, it will be understood that the electrodes may be spaced at different intervals on each arm without departing from the scope of the disclosure. That is, for example only and without limitation, in various embodiments, electrodes on first outboard 103 may be spaced closer together or further apart than electrodes on first inboard arm 104. While the electrodes are shown as substantially evenly distributed on arms 103, 104, 105 and 106, it will be understood that the electrodes may be unevenly spaced intervals on each arm without departing from the scope of the disclosure. That is, for example only and without limitation, in various embodiments, the electrodes may be located on the arms such that the electrodes are closer together near the distal end of flexible tip portion 110 and further apart near the proximal end of flexible tip portion 110. Alternatively, for example only and without limitation, in various embodiments, the electrodes may be located on the arms such that the electrodes are farther apart near the distal end of flexible tip portion 110 and closer together near the proximal end of flexible tip portion 110.

In some embodiments, the partially-masked electrodes 42 can be used in diagnostic, therapeutic, and/or mapping procedures. For example and without limitation, the partially-masked electrodes 42 can be used for electrophysiological studies, pacing, cardiac mapping, and ablation. In some embodiments, the partially-masked electrodes 42 can be used to perform unipolar or bipolar ablation. This unipolar or bipolar ablation can create specific lines or patterns of lesions. In some embodiments, the partially-masked electrodes 42 can receive electrical signals from the heart, which can be used for electrophysiological studies. In some embodiments, the partially-masked electrodes 42 can perform location or position sensing functions related to cardiac mapping.

In some embodiments, the high density electrode assembly 101 can include a catheter shaft 107. The catheter shaft 107 can include a proximal end and a distal end. The proximal end of catheter shaft 107 may be connected to or integrally formed with the distal end 28 of shaft 24 of catheter 18, as shown in FIG. 2, in place of electrode assembly 30. That is, the distal tip assembly of the basket electrode assembly 30 may be swapped with, interchanged with, or substituted with the distal tip assembly of the high density electrode assembly 101. The distal end can include a connector 108, which can couple the distal end of the catheter shaft 107 to a proximal end of the planar array. The catheter shaft 107 can define a catheter shaft longitudinal axis aa, as depicted in FIG. 11, along which the first outboard arm 103, first inboard arm 104, second inboard arm 105, and second outboard arm 106 can generally extend parallel in relation therewith. The catheter shaft 107 can be made of a flexible material, such that it can be threaded through a tortuous vasculature of a patient. In some embodiments, the catheter shaft 107 can include one or more ring electrodes 111 disposed along a length of the catheter shaft 107. The ring electrodes 111 can be used for diagnostic, therapeutic, and/or mapping procedures, in an example. In various embodiments, ring electrodes 111 may be partially-masked in the same manner as partially-masked electrodes 42. In other embodiments, ring electrodes 111 may be un-masked. In yet other embodiments, the high density electrode assembly 101 may include a combination of partially-masked, unmasked, or fully masked ring electrodes.

The flexible tip portion 110 can be adapted to conform to tissue (e.g., cardiac tissue). For example, when the flexible tip portion 110 contacts tissue, the flexible tip portion can deflect, allowing the flexible framework to conform to the tissue. In some embodiments, the arms (or the understructure of the arms) comprising the paddle structure (or multi-arm, electrode-carrying, flexible framework) at the distal end of the catheter depicted in FIG. 11 is preferably constructed from a flexible or spring-like material such as Nitinol and/or a flexible substrate, as discussed herein. The construction (including, for example, the length and/or diameter of the arms) and material of the arms can be adjusted or tailored to create, for example, desired resiliency, flexibility, foldability, conformability, and stiffness characteristics. These characteristics may vary from a proximal end to a distal end of an arm, or between or among the plurality of arms comprising a single paddle structure. The foldability of materials such as Nitinol and/or flexible substrate provide the additional advantage of facilitating insertion of the paddle structure into a delivery catheter or introducer, whether during delivery of the catheter into the body or removal of the catheter from the body at the end of a procedure.

Another embodiment of a distal tip assembly comprises a planar array of partially-masked electrodes, wherein the distal tip assembly is a high density electrode assembly 201 of the disclosure is illustrated in FIG. 12 and is described below. Some features of high density electrode assemblies 201 and 101 are common to one another and, accordingly, descriptions of such features in one embodiment should be understood to apply to the other embodiment. Furthermore, particular characteristics and aspects of one embodiment may be used in combination with, or instead of, particular characteristics and aspects of another embodiment.

FIG. 12 illustrates another embodiment of a high density electrode assembly 201 which includes a variety of partially-masked and un-masked electrodes. Other than the differences in the electrodes, high density electrode assembly 201 is substantially the same or identical to high density electrode assembly 101. High density electrode mapping catheter 201 includes a population of partially-masked electrodes having different sized openings. For example only and without limitation, first outboard arm 103 includes four partially-masked electrodes 42a each having an opening 58a, first inboard arm 104 includes four partially-masked electrodes 42b each having an opening 58b smaller than opening 58a, and second inboard arm 105 includes four partially-masked electrodes 42c each having an opening 58c smaller than openings 58a and 58b. In an embodiment, for example only and without limitation, opening 58a may have a diameter about 0.031 mm, opening 58b may have a diameter about 0.022 mm, and opening 58c may have a diameter about 0.014 mm. Although the openings 58a, 58b, and 58c are shown as having an oval shape, it will be understood that openings 58a, 58b, and 58c may have other shapes, with or without rounded edges or corners, without departing from the scope of the disclosure, including, for example only and without limitation, a circle, an ellipse, a diamond, a rectangle, a hexagon, a square, a pentagon, an irregular polygon, a triangle. Openings 58a, 58b, and 58c may be of different sizes without departing from the scope of the disclosure. Additionally, in various embodiments, for example only and without limitation, second outboard arm 106 of high density electrode assembly 201 includes four un-masked electrodes 16. In other embodiments, for example only and without limitation, second outboard arm 106 may include partially-masked electrodes having openings of a different shape and/or size from openings 58a, 58b, and 58c.

High density electrode assembly 201 may be used as a test bed for testing one or more parameters, such as for example only and without limitation: opening 58 shapes, opening 58 sizes, coating 56 thickness, coating material, electrode spacing, distribution, and number of electrodes (masked, unmasked, and partially masked).

While the partially-masked electrodes shown and described herein are ring electrodes, it will be understood that printed or flex circuit electrodes may be partially-masked without departing from the scope of the disclosure. Thus, the embodiment of FIGS. 13-15 incorporate partially-masked flex circuit electrodes 342 into a distal tip. Some features of partially-masked flex circuit electrodes 34 and partially-masked electrodes 42 are common to one another and, accordingly, descriptions of such features in one embodiment should be understood to apply to other embodiments. Furthermore, particular characteristics and aspects of one embodiment may be used in combination with, or instead of, various aspects of another embodiment.

Figure 13:
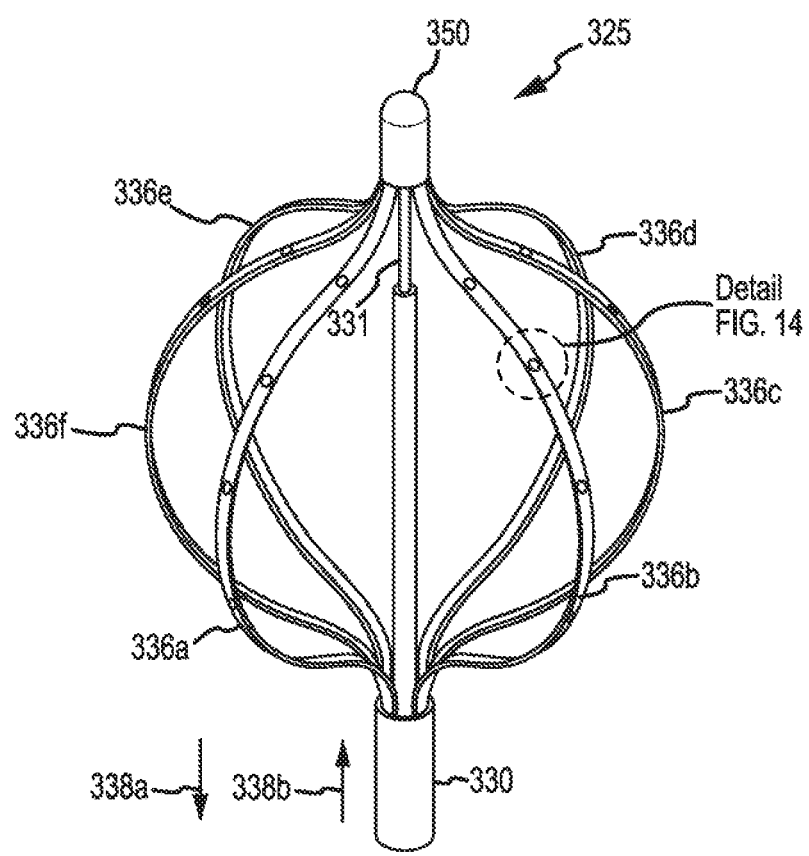
FIG. 13 is an isometric view of a distal tip assembly comprising a basket electrode assembly having partially-masked flex circuit electrodes, according to another embodiment of the disclosure.
Figure 14:
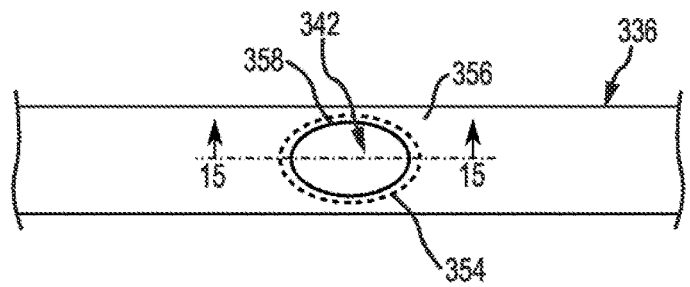
FIG. 14 is an enlarged view of the region in the dashed circle labeled "FIG. 14" in FIG. 13, depicting a partially-masked electrode on a section of a spline of the basket electrode assembly depicted in FIG. 13.

With reference to FIG. 13, a distal tip assembly comprising a basket electrode assembly 325 is shown having a plurality of partially-masked flex circuit electrodes 342 (as shown in FIG. 14) which are oriented to contact tissue of interest. Basket electrode assembly 325 is shown with the basket portion of the catheter in an expanded configuration.

Basket electrode assembly 325 is shown as it may include an outer tubing 330 housing, a deployment member 331, and a terminal end 350. The outer tubing 330 of basket electrode assembly 325 may be connected to, or integrally formed with, the distal end 28 of shaft 24 of catheter 18, as shown in FIG. 2 (in place of electrode assembly 30). Basket electrode assembly is shown having splines 336a-f; however, the basket catheter 325 is not limited to any particular number of splines 336, as will be readily understood by those having ordinary skill in the art after becoming familiar with the teachings herein. Additional features and structure of basket electrode assembly are shown and described in U.S. patent application Ser. No. 15/333,798 (published as U.S. Patent Application Pub. No. 2017/0100075) the entire disclosure of which is incorporated by reference as though fully set forth herein.

Each spline 336 is connected at the proximal end of the splines 336 to the outer tubing 330, and each spline 336 is connected at the opposite or distal end of the splines 336 to the deployment member 331. The deployment member 331 is operable to be moved in a first direction (e.g., in the direction of arrow 338a) relative to the outer tubing 330 to expand the splines 336 to a deployed position, as shown in FIG. 13. The deployment member 331 is also operable to be moved in a second direction (e.g., in the direction of arrow 338b) relative to the outer tubing 330 to collapse the splines 336 to an undeployed position.

The deployment member 331 may include a pull wire. The deployment member 331 may be a solid stainless steel or Nitinol wire. Alternatively, the deployment member 331 may be a hollow tube (or configured to house tubing). The deployment member 331 should be manufactured to be sufficiently stiff such that the deployment member 331 can be operated remotely (e.g., outside of the patient's body), and be moved in the directions illustrated by arrows 338a and 338b to expand and contract the splines 336.

In any event, the basket electrode assembly 325 may be inserted into a catheter shaft (e.g., sheath (not shown) in its undeployed position for placement in the patient's body (e.g., within a heart chamber). The basket electrode assembly 325 may then be expanded to its deployed position for a medical procedure within the patient's body. Following the procedure, the basket electrode assembly 325 may again be collapsed to its undeployed position so that the basket electrode assembly 325 may be withdrawn from the patient.

Figure 15:
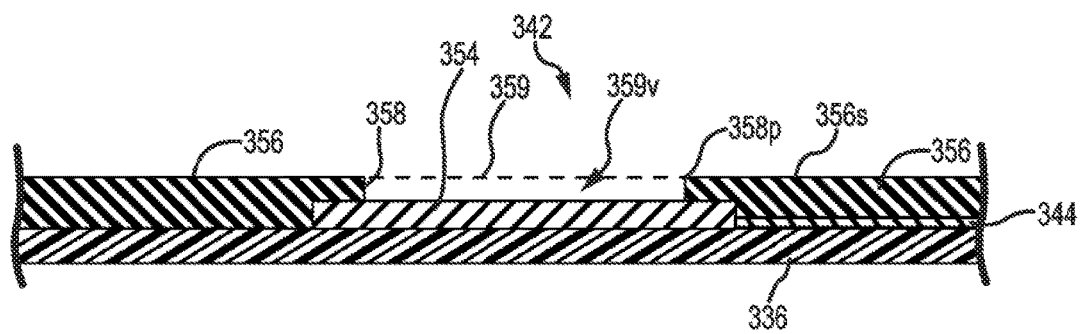
FIG. 15 is an enlarged, cross-sectional view of the partially-masked flex circuit electrode depicted in FIGS. 13 and 14 taken along line 15-15 of FIG. 14.

In various embodiments, for example only and without limitation, the splines 336 are formed from sheets. The sheets can be formed of a suitable flexible material such as plastic (e.g., polyimide) or metal (e.g., platinum, gold, stainless steel, iridium, or alloys of these metals). As shown in FIGS. 13, 14 and 15, a population of spaced apart partially-masked flex circuit electrodes 342 and corresponding electrode traces 344 (as shown in FIG. 14) are provided on the splines 336. With specific reference to FIG. 15 the partially-masked flex circuit electrodes 342 may be formed of a conductive material 354 which may be printed, adhered, bonded, etched or otherwise provided on the splines 336, which may serve as a substrate for the partially-masked flex circuit electrodes 342.

The traces 344 may then be connected to electrical wiring and extend through a catheter (e.g., catheter 18 shown in FIG. 2). The electrical wiring may convey electrical signals between the partially-masked flex circuit electrodes 342 and one or more control system (not shown). For example, the electrical signals may be used to control output of ablation electrodes, or for processing input from mapping electrodes for viewing or storage by the user (e.g., on an electrical monitoring device).

The conductive material 354 may be composed of platinum, gold, stainless steel, iridium, or alloys including one or more of these metals, or other biocompatible, electrically-conductive material. As shown in FIG. 15, an electrically-insulating, polymer surface coating 356 may be applied to each spline 336 and the conductive material 354. The surface coating 356 may be formed of a material with high dielectric properties that can be applied in a very thin layer. Exemplary surface coatings may include thin coatings of polyester, polyamides, polyimides, and blends of polyurethane and polyimides. In one embodiment, for example only and without limitation, surface coating 356 may be Parylene. In various embodiments, for example only and without limitation, the thickness of the surface coating 356 may range from about 0.0001 mm to about 0.05 mm. In other embodiments, for example only and without limitation, the thickness of the surface coating 356 may range from about 0.0003 mm to about 0.0006 mm.

An aperture is formed in the surface coating 356 to create a contoured opening 358 that exposes or reveals a small area of the conductive band 354. The contoured opening 358 may be formed by laser, chemical, or other material removing or etching process to remove a portion of the surface coating 356 to expose the conductive band 354 underneath. The edges or corners of the contoured opening 358 may be curved, rounded, or otherwise contoured to minimize any edge effects that could arise due to the imposition of a sharp edge, corner, or point. In various embodiments, for example only and without limitation, the openings 358 are oriented on the partially-masked electrodes 342 such that when the splines 336 of basket electrode assembly 325 are expanded, the openings 358 are facing the tissue of interest, such that they can contact the tissue of interest. In other embodiments, for example only and without limitation, the openings 358 are oriented on the partially-masked electrodes 342 such that when the splines 336 of basket electrode assembly 325 are expanded, the openings 358 may be maneuvered or oriented such that they are facing the tissue of interest and can contact the tissue of interest.

Although the contoured opening 358 is shown as having an oval shape, it will be understood that opening 358 may have other shapes, with or without rounded edges or corners, without departing from the scope of the disclosure, including, for example only and without limitation, a circle, an ellipse, a diamond, a rectangle, a hexagon, a square, a pentagon, an irregular polygon, a triangle. Opening 358 may be of different sizes without departing from the scope of the disclosure. For example only and without limitation, where opening 358 is a circle, the diameter of the opening 358 may range from about 0.010 mm to about 0.050 mm. In one embodiment, for example only and without limitation, the diameter of the opening 358 may be about 0.014 mm. In another embodiment, for example only and without limitation, the diameter of the opening 358 may be about 0.022 mm. In yet another embodiment, for example only and without limitation, the diameter of the opening 358 may be about 0.031 mm. Moreover, although a single opening 358 is shown per partially-masked flex circuit electrode 342, it will be understood that each partially-masked flex circuit electrode 342 may include more than one opening 358 (e.g., 2, 3, 4, or more) without departing from the scope of the disclosure.

As shown in FIG. 15, opening 358 has an upper perimeter 358p at the outer surface 356s of the surface coating 356. The upper perimeter 358p of opening 358 defines an imaginary boundary area 359 above the exposed area of the conductive material beyond which no part of the exposed conductive material 354 extends. The imaginary boundary area 359 is a planar surface having an outer edge(s) which is/are coincident and coextensive with the upper perimeter 358p of opening 358. Therefore partially-masked flex circuit electrode 342 includes a gap or void 359v between imaginary boundary area 359 and conductive band 354.

Figure 16:
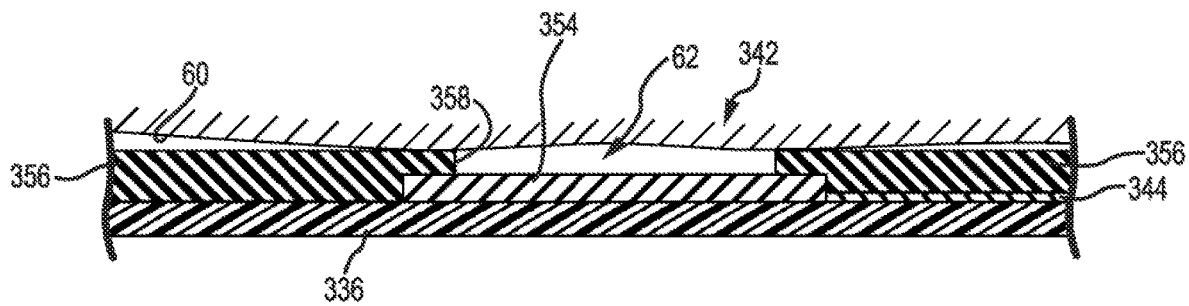
FIG. 16 is a cross-sectional view of a partially-masked flex circuit electrode of FIGS. 13-15 positioned against a tissue of interest.

Referring now to FIG. 16, partially-masked flex circuit electrode 342 is shown interfacing with the surface 60 of a tissue of interest. The surface coating 356 is between the conductive material 354 and the surface 60 of the tissue of interest and because no part of conductive material 354 extends beyond the imaginary boundary area 359 shown in FIG. 15, a void 62 is created between the conductive material 354 and the surface 60 of the tissue of interest at the location of the opening 358 in the surface coating 356. It is desirable to have the void 62 be as small as possible to increase the signal received by the partially-masked flex circuit electrode 342. Thus, if the surface 60 of the tissue is touching the conductive material 354 the received signal may be increased. In some embodiments, for example only and without limitation, an electrical signal may be emitted by the partially-masked flex circuit electrode 342 to attract the surface 60 of the tissue toward the conductive material 354.

The raised surface coating 356, which is between the conductive material 354 and the surface 60, creates a cupped or cup-like profile at the opening 358 which isolates the conductive material 354 of the partially-masked flex circuit electrode 342 from the conductive path through the blood pool. That is, when the upper perimeter 358p of the raised surface coating 356 is in contact with the tissue of interest, the surface coating 356 creates a seal between the blood pool and the opening 358 so that no blood in the blood pool can contact conductive material 354. When the opening 358 is oriented toward the tissue of interest and the surface coating 356 around the perimeter of the opening 358 makes contact with the surface 60 of the tissue of interest, the conductive band 354 is completely isolated or sealed from any far field effects present in the blood pool. This will be even more effective in rougher tissue (e.g., ventricle) than in smother tissue (e.g., atria). Thus, except for opening 358, partially-masked flex circuit electrode 342 has no other open conductive ends or portions as with typical ring electrodes. This results in a more focused electrode as compared to unmasked electrodes. Aspects of the present disclosure are desirable to minimize the volume of the void 62 while maintaining the seal from the blood pool provided by surface coating 356.

By completely isolating partially-masked flex circuit electrode 342 from any far field effects present in the blood pool, the noise from the far field effects is significantly reduced or eliminated. This increases the signal to noise ratio of the electrical signal measured by the partially-masked flex circuit electrode 342. Because the far field effects are no longer measured by the partially-masked electrode 342, the signal quality and magnitude of the measured (weak) local electrical signals from unhealthy tissue is improved as compared to a typical un-insulated ring electrode 16. This also allows for easier identification, locating, detecting and/or diagnosing unhealthy tissue.

Figure 17:
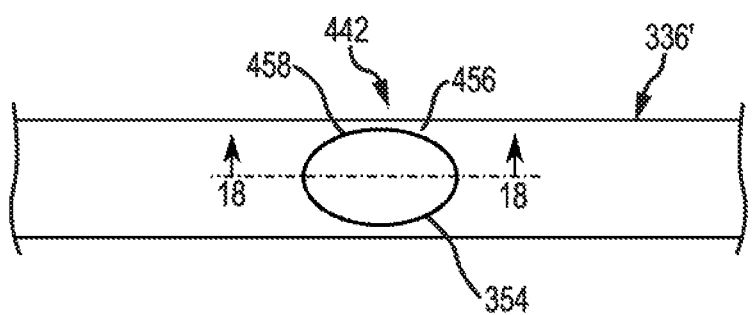
FIG. 17 is a plan view of a partially-masked flex circuit electrode according to another embodiment of the disclosure.
Figure 18:
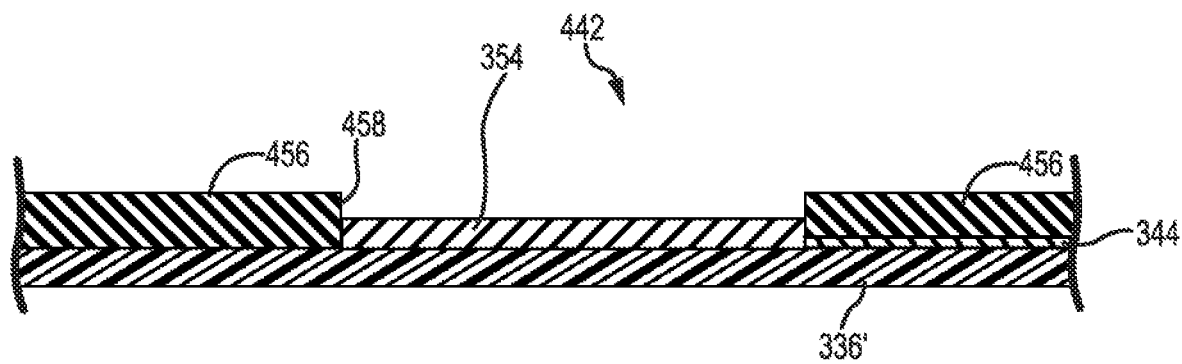
FIG. 18 is a cross-sectional view of a partially-masked flex circuit electrode of FIG. 17 taken along line 18-18 of FIG. 17.

Another embodiment of a partially-masked flex circuit electrode 442 of the disclosure is illustrated in FIGS. 17 and 18 and is described below. Some features of partially-masked flex circuit electrode 442 and 342 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

With further reference to FIGS. 17 and 18, a spline 336' is shown with a conductive material 354 which may be printed, adhered, bonded, etched, or otherwise provided on the spline 336'. Additionally, an electrically-insulating, polymer surface coating 456 may be applied to each spline 336'. However, unlike partially-masked flex circuit electrode 342 shown in FIGS. 14-16, the surface coating 456 is not applied on top of conductive material 354, or is fully removed from conductive material, such that opening 458 in the surface coating 456 has the same area as conductive material 354. Thus, as shown in FIG. 18, surface coating 456 abuts, but does not overlap, conductive material 354.

Figure 19:
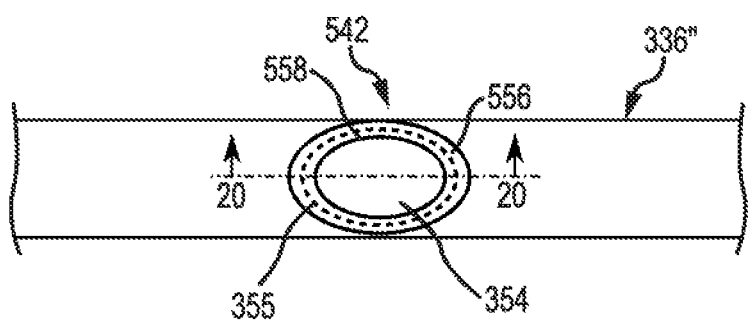
FIG. 19 depicts a plan view of a partially-masked flex circuit electrode according to another embodiment of the disclosure.
Figure 20:
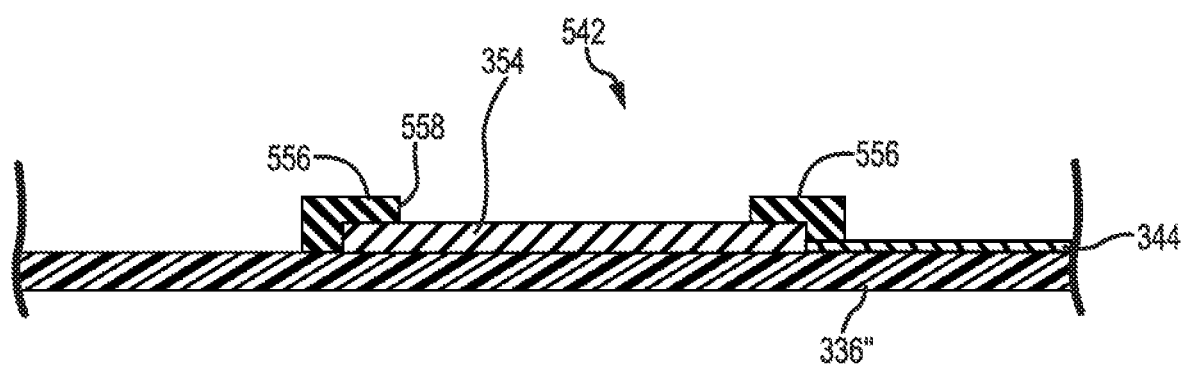
FIG. 20 is a cross-sectional view of the partially-masked flex circuit electrode of FIG. 19 taken along line 20-20.

Another embodiment of a partially-masked flex circuit electrode 542 of the disclosure is illustrated in FIGS. 19 and 20 and is described below. Some features of partially-masked flex circuit electrode 542 and 342 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

With further reference to FIGS. 19 and 20, a spline 336" is shown with a conductive material 354 which may be printed, adhered, bonded, etched or otherwise provided on the spline 336". The conductive material 354 has an outer perimeter or outer edge defined by dashed line 355 in FIG. 19. In this embodiment, as in several of the other embodiments described herein, the outer perimeter 355 is an ellipsoid, but may define other shapes, including irregular shapes. Additionally, an electrically-insulating, polymer surface coating 556 may be applied to each spline 336" locally around conductive material 354. That is, unlike partially-masked flex circuit electrodes 342 and 442 shown in FIGS. 14-16 and 17-18, the surface coating 556 is only applied proximate to the outer perimeter 355 of conductive material 354. Thus, surface coating 556 surrounds the outer edges or sides of conductive material 354 and projects above conductive material 354 but does not otherwise cover all of spline 336". Surface coating 556 therefore only rings around conductive material 354. An opening 558 smaller than the area of conductive material 354 is provided in surface coating 556.

Figure 21:
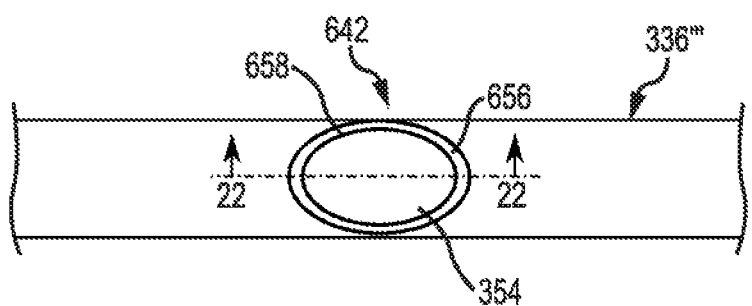
FIG. 21 depicts a plan view of a partially-masked flex circuit electrode according to another embodiment of the disclosure.
Figure 22:
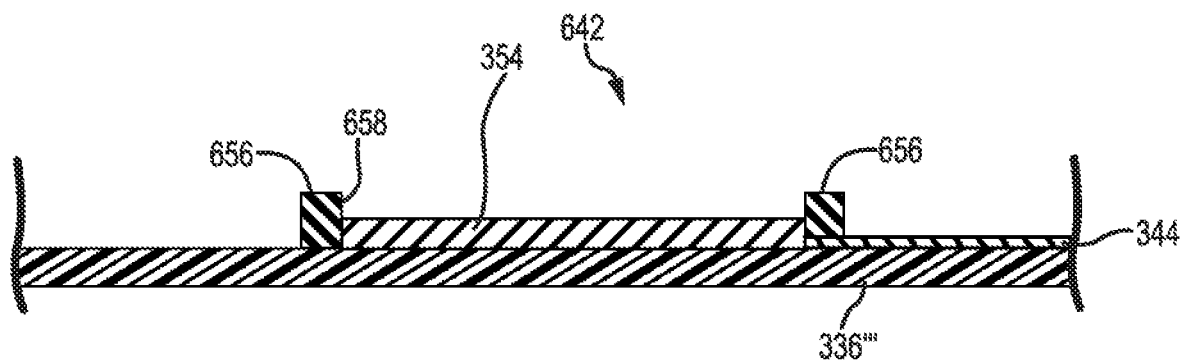
FIG. 22 depicts a cross-sectional view of the partially-masked flex circuit electrode of FIG. 21 taken along line 22-22.

Another embodiment of a partially-masked flex circuit electrode 642 of the disclosure is illustrated in FIGS. 21 and 22 and is described below. Some features of partially-masked flex circuit electrode 642, 542, 442, and 342 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

With further reference to FIGS. 21 and 22, a spline 336''' is shown with a conductive material 354 which may be printed, adhered, bonded, etched, or otherwise provided on the spline 336''. Additionally, an electrically-insulating, polymer surface coating 656 may be applied to each spline 336''' locally around conductive material. That is, unlike partially-masked flex circuit electrodes 342 and 442 shown in FIGS. 14-16 and 17-18, the surface coating 656 is only applied proximate conductive material 354. Thus, surface coating 656 surrounds the sides of conductive material 354 and projects above conductive material 354 but does not otherwise cover all of spline 336. Surface coating 656 therefore only rings around conductive material 354. Moreover, like opening 458 (see FIGS. 17 and 18) of partially-masked flex circuit electrode 442, the surface coating 656 is not applied on top of conductive material 354, or is fully removed from conductive material, such that opening 658 in the surface coating 656 has the same area as conductive material 354. Thus, as shown in FIG. 22, surface coating 656 abuts, but does not overlap, conductive material 354.

While the partially-masked electrodes described herein are described as being oriented and/or maneuvered such that they contact the tissue of interest, it will be understood that in various embodiments for example, additional un-masked and/or partially-masked electrodes may be provided which are oriented such that they do not contact the tissue of interest. These non-contact electrodes may be electrically connected with conductors or leads separately from the conductors or leads to the partially-masked electrodes which contact the tissue of interest. Thus, these electrically separate non-contact electrodes may be used to sense the blood pool and/or far field effects separately from the tissue local field. This arrangement is described in greater detail in PCT Application No. PCT/US2016/058244 (published as WO/2017/070559), the entire disclosure of which is incorporated by reference as though fully set forth herein.

Although the partially-masked electrodes described herein are shown as being used in basket electrode assemblies and high density electrode assemblies, it will be understood that the partially-masked electrodes can be used in any type and shape of distal tip assembly for a catheter, including for example only and without limitation, a catheter having a single distal tip assembly which may be steerable.

Additionally, in the various embodiments described herein, the insulated surface coating material, the insulated surface coating thickness, and/or the insulated surface coating location may be selected and configured to allow repeated opening and closing of the splines of the basket electrode assemblies and repeated flexure of the arms of the high density electrode assemblies described herein without cracking, flaking, breaking and/or other failure of the insulated surface coating. This aids durability, longevity and/or reliability of the distal tip assembly having the partially-masked electrodes. Such aspects also reduce the potential for the insulated surface coating to be released from the distal tip assembly and remaining in a patient. Moreover, the surface coating material, the surface coating thickness, and/or the insulated surface coating location may be selected and configured such that the insulated surface coating does not impede or inhibit the opening and closing of the splines of the basket electrode assemblies or the flexure of the arms of the high density electrode assembly described herein. For example, the localized insulated surface coating is only proximate the conductive material as shown in FIGS. 19-22. Because the insulated surface coating is only proximate the conductive material, the impact of the insulated surface coating on the opening and closing of the splines is reduced or eliminated. Additionally, due to a potential increased stiffness of the spline proximate the conductive material, the localized insulated surface coating is less likely to flex during the opening and closing of the splines. The localized insulated surface coating is thus potentially subject to lower stresses and strains as compared to an insulated surface coating along the entire spline (see e.g., FIGS. 14-18).

While clinical benefits of the partially-masked electrodes have been described herein, the use of the insulated surface coatings to partially mask electrodes may also provide manufacturing advantages. For example only and without limitation, because a surface coating is applied to an electrode and an opening is made to expose a portion of the conductive material of the electrode, the manufacturing tolerances of the conductive material may be reduced. That is, the size of the conductive material does not need to be held to such a tight tolerance because the effective size of the conductive area of the electrode will be determined by the size of the opening in the surface coating. This may allow the use of a common size of conductive material for different applications, wherein the size of the opening is varied for the particular application. This may also reduce manufacturing costs and time.

Among other things, the disclosed catheters, with their plurality of partially-masked electrodes, are useful to (1) define regional propagation maps of particularly sized areas (e.g., one centimeter square areas) within the atrial walls of the heart; (2) identify complex fractionated atrial electrograms for ablation; (3) identify localized, focal potentials between the microelectrodes for higher electrogram resolution; and/or (4) more precisely target areas for ablation. These mapping catheters and ablation catheters are constructed to conform to, and remain in contact with, cardiac tissue despite potentially erratic cardiac motion. Such enhanced stability of the catheter on a heart wall during cardiac motion provides more accurate mapping and ablation due to sustained tissue electrode contact. Additionally, the catheters described herein may be useful for epicardial and/or endocardial use. For example, the planar array embodiments depicted herein may be used in an epicardial procedure where the planar array of partially-masked electrodes is positioned between the myocardial surface and the pericardium. Alternatively the planar array embodiments may be used in an endocardial procedure to quickly sweep and/or analyze the inner surfaces of the myocardium and quickly create high-density maps of the heart tissue's electrical properties.

Figure 23:
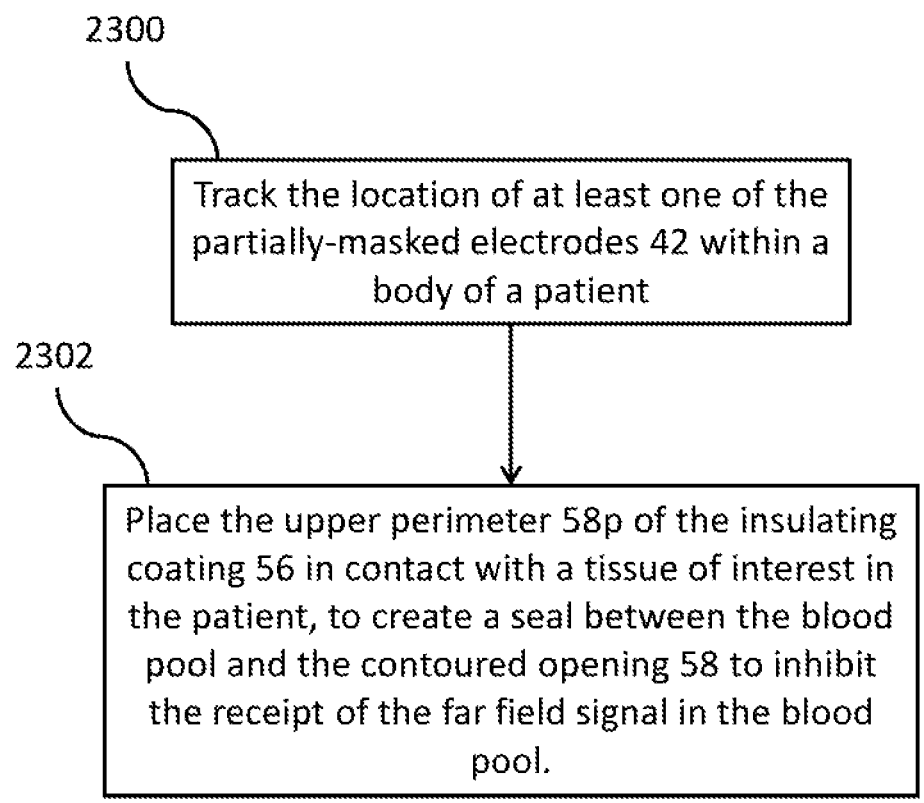
FIG. 23 is a flowchart illustrating a method of using catheters having partially-masked electrodes according to various embodiments of the disclosure.

Now with reference to FIG. 23, a method of using catheters having the partially-masked electrodes described herein is shown and described. At step 2300, the method includes tracking the location of at least one of the partially-masked electrodes 42 within a body of a patient. The insulated coating 56 of at least one of the partially-masked electrodes 42 is selected and configured to allow the reception of a localization signal by the conductive material 54, as described herein. The insulated coating 56 of at least one of the partially-masked electrodes 42 is selected and configured to prevent the reception of at least a significant amount of a far field signal by the conductive material 54. The method further includes, at step 2302, placing the upper perimeter 58p of the insulated coating 56 of at least one of the partially-masked electrodes 42 in contact with a tissue of interest in the body of the patient, the tissue of interest being proximate a blood pool, such that the insulated coating 56 creates a seal between the blood pool and the contoured opening 58 to inhibit the receipt of the far field signal in the blood pool.

Figure 24A:
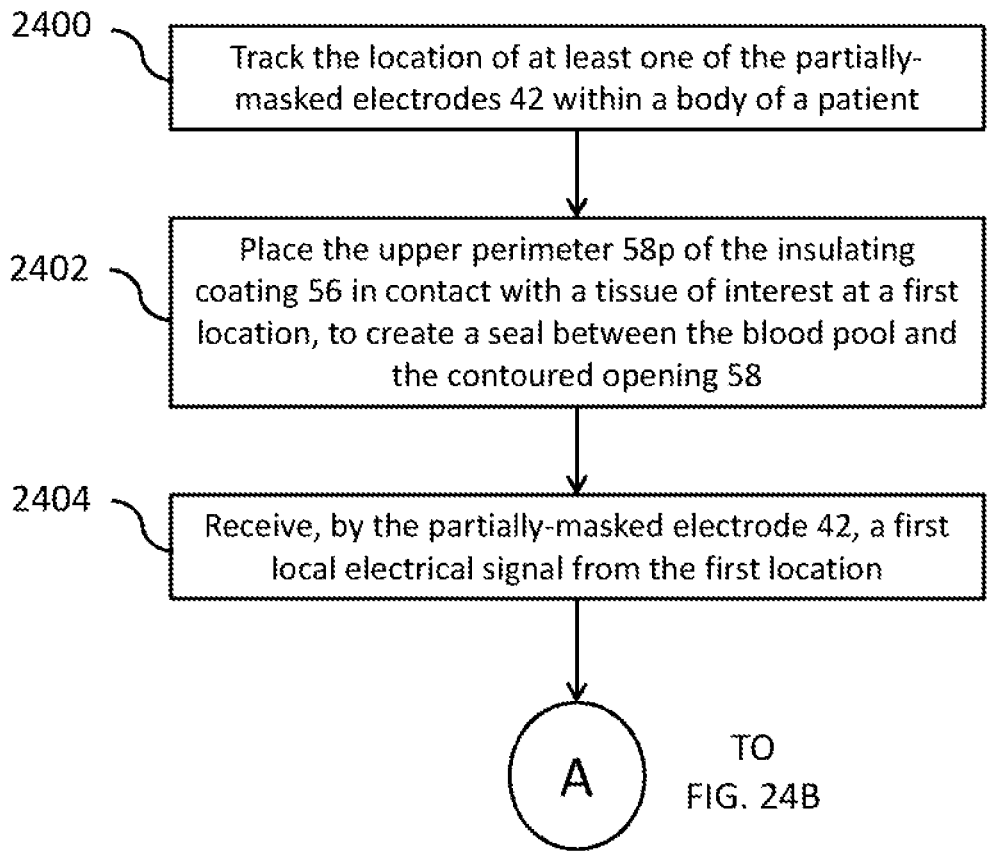
FIGS. 24A-24B are flowcharts illustrating another method of using catheters having partially-masked electrodes according to various embodiments of the disclosure.
Figure 24B:
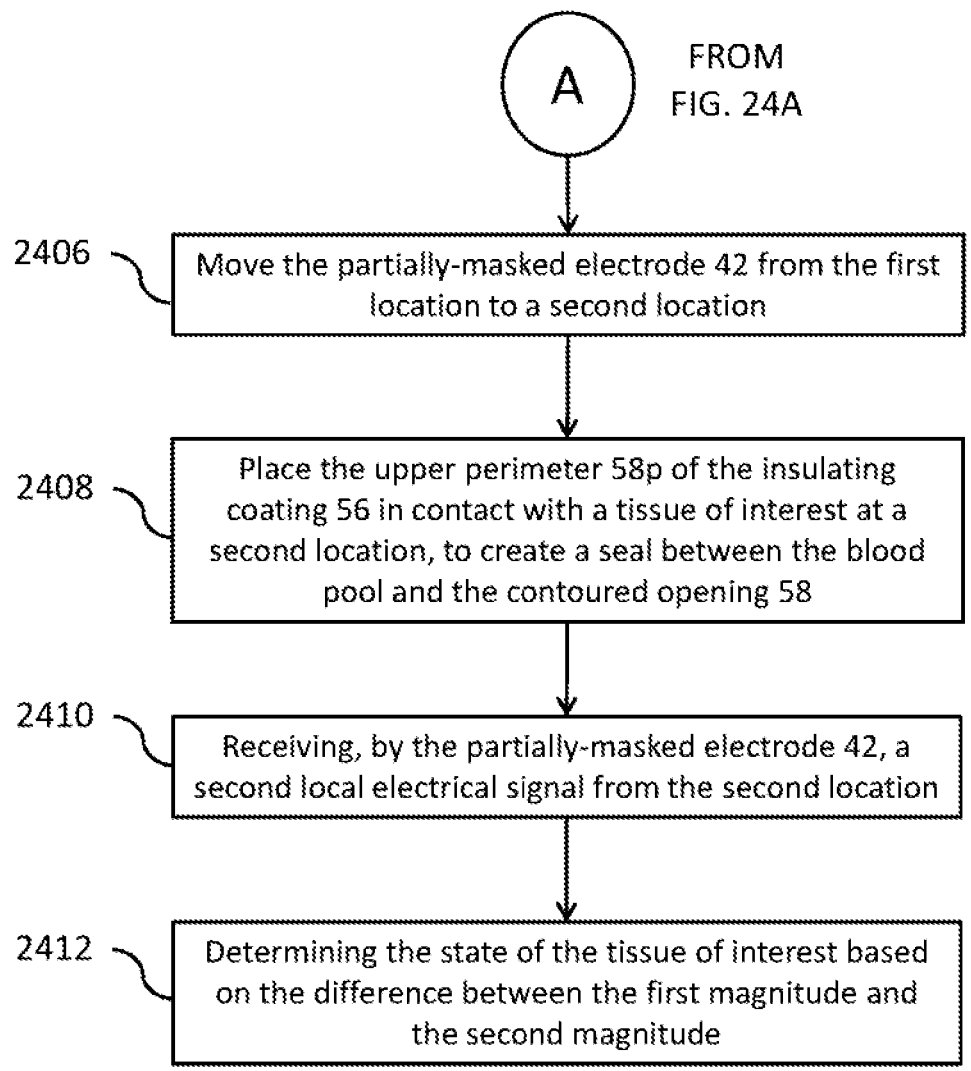

Now with reference to FIGS. 24A and 24B, another method of using catheters having the partially-masked electrodes described herein is shown and described. At step 2400, the method includes tracking the location of one of the partially-masked electrodes 42 within a body of a patient. The insulated coating 56 of the partially-masked electrode 42 is selected and configured to allow the reception of a localization signal by the conductive material 54, as described in greater detail elsewhere herein. The insulated coating 56 of the partially-masked electrode 42 is selected and configured to prevent the reception of at least a significant amount of a far field signal by the conductive material 54. At step 2402, the method further includes placing the upper perimeter 58p of the insulated coating 56 of the partially-masked electrode 42 in contact with a tissue of interest at a first location in the body of the patient, the tissue of interest being proximate a blood pool, such that the insulated coating 56 creates a seal between the blood pool and the contoured opening 58 to inhibit the receipt of the far field signal in the blood pool. At step 2404, the method further includes receiving, by the partially-masked electrode 42, a first local electrical signal from the first location on the tissue of interest at the contoured opening 58. The first local electrical signal having a first magnitude, wherein as a result of the seal between the blood pool and the contoured opening the first local electrical signal comprises little or no far field signal.

As shown in FIG. 24B, the method may continue, at step 2406, with moving the partially-masked electrode 42 from the first location to a second location in the body of the patient. At step 2408, the method may further include placing the upper perimeter 58p of the insulated coating 56 of the partially-masked electrode 42 in contact with the tissue of interest at the second location in the body of the patient. The tissue of interest being proximate a blood pool, such that the insulated coating 56 creates a seal between the blood pool and the contoured opening 58, and thereby inhibits the receipt of the far field signal in the blood pool. Then at step 2410, the method may further include, receiving, by the partially-masked electrode 42, a second local electrical signal from the second location on the tissue of interest at the contoured opening 58. The second local electrical signal having a second magnitude, wherein as a result of the seal between the blood pool and the contoured opening the second local electrical signal comprises little or no far field signal. In various embodiments, the second local electrical signal may have a second magnitude different from the first magnitude of the first local electrical signal. Then at step 2412, the method may further include diagnosing the health of the tissue of interest based on the difference between the first magnitude and the second magnitude. That is, the state (e.g., voltage magnitude) of the tissue can be determined and an assessment of the health of the tissue may be able to be made based on the measured state.

In some embodiments consistent with the present disclosure, one or more partially-masked electrodes may be oriented inward (away from the tissue) relative to the catheter. Accordingly, these inward oriented partially-masked electrodes are solely exposed to a blood pool and receives signals from the blood pool indicative of "far field" influences. Controller circuitry may utilize the signal from such inward oriented partially-masked electrodes to filter out such "far field" influences from the signals received from outward facing partially-masked electrodes in contact with the tissue.

Although several embodiments of an apparatus, system, and method in accordance with present teachings have been described above with a certain degree of particularity, those skilled in the art could make numerous alterations to the disclosed embodiments without departing from the scope of this disclosure. All directional references (e.g., upper, lower, upward, downward, left, right, leftward, rightward, top, bottom, above, below, vertical, horizontal, clockwise and counterclockwise) are only used for identification purposes to aid the reader's understanding of the disclosed embodiments, and do not create limitations, particularly as to the position, orientation, or use of the disclosed embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the present teachings as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A partially-masked electrode comprising:
a conductive material; and
an insulated coating having an outer surface;
wherein the insulated coating defines a contoured opening that exposes an area of the conductive material,
wherein the contoured opening has a perimeter at the outer surface of the insulated coating;
wherein an entirety of the perimeter of the opening is offset above the exposed area of the conductive material;
wherein edges along the perimeter of the insulated coating are rounded to minimize edge effects due to imposition of corners; and wherein the insulated coating is relatively thicker around the contoured opening to facilitate a reception of a localization signal by the partially masked electrode.

2. The partially-masked electrode of claim 1, wherein the partially-masked electrode comprises a ring electrode and the exposed area of the conductive material is a surface that extends radially about a longitudinal axis of the ring electrode.

3. The partially-masked electrode of claim 1, wherein the exposed area of the conductive material is 0.25 mm$^2$.

4. The partially-masked electrode of claim 1, wherein the contoured opening is circular in shape and extends through the insulated coating normal to the exposed area of the conductive material.

5. The partially-masked electrode of claim 4, wherein the diameter of the contoured opening ranges from 0.010 mm to 0.050 mm.

6. The partially-masked electrode of claim 4, wherein the diameter of the contoured opening is 0.014 mm.

7. The partially-masked electrode of claim 4, wherein the diameter of the contoured opening is 0.022 mm.

8. The partially-masked electrode of claim 4, wherein the diameter of the contoured opening is 0.031 mm.

9. The partially-masked electrode of claim 1, wherein the insulated coating has a thickness ranging from 0.0003 mm to 0.0006 mm; and wherein the offset between the perimeter of the opening and the exposed area of the conductive material is the thickness of the insulated coating.

10. The partially-masked electrode of claim 1, wherein the perimeter of the insulated coating is configured and arranged to be placed in contact with a tissue of interest, the tissue of interest being proximate a blood pool, the insulated coating configured to create a seal between the blood pool and the contoured opening so that no blood in the blood pool can contact the conductive material.

11. The partially-masked electrode of claim 1, wherein the insulated coating is configured to facilitate a reception of a localization signal by the conductive material and to mitigate a reception of at least a portion of a far field signal by the conductive material.

12. A catheter, comprising:
an elongate, deformable shaft comprising a proximal end and a distal end; and a distal tip assembly coupled to said distal end of said shaft, said distal tip assembly comprising a plurality of partially-masked electrodes disposed thereon;
wherein at least one of the plurality of partially-masked electrodes comprises a conductive material and an insulated coating having an outer surface,
wherein the insulated coating defines a contoured opening that exposes an area of the conductive material;
wherein the contoured opening has a perimeter at the outer surface of the insulated coating, and wherein an entirety of the perimeter of the opening is offset above the exposed area of the conductive material; and
wherein the insulated coating is relatively thicker around the contoured opening to facilitate a reception of a localization signal by the partially masked electrode.

13. The catheter of claim 12, wherein at least one of the plurality of partially-masked electrodes comprises a ring electrode.

14. The catheter of claim 12, wherein the distal tip assembly is a basket electrode assembly, the basket electrode assembly coupled to said distal end of said shaft, the basket electrode assembly further includes a proximal end and a distal end, and a first spline with the plurality of partially-masked electrodes disposed thereon, the basket electrode assembly is configured to assume a compressed state and an expanded state.

15. The catheter of claim 12, wherein the distal tip assembly comprises a high density electrode assembly.

16. The catheter of claim 12, wherein the perimeter of the insulated coating is placed in contact with a tissue of interest, the tissue of interest being proximate a blood pool, the insulated coating configured and arranged to create a seal between the blood pool and the contoured opening so that no blood in the blood pool contacts the conductive material.

17. The catheter of claim 12, wherein at least one of the plurality of partially-masked electrodes comprises a flex printed electrode.

18. The catheter of claim 12, wherein the distal tip assembly is a flexible tip portion including a flexible framework, the plurality of partially-masked electrodes are disposed on the flexible framework and form a flexible array of partially-masked electrodes configured to conform to tissue.

19. The catheter of claim 12, wherein the insulated coating is configured to isolate the conductive material and to mitigate a reception of at least a portion of a far field signal by the conductive material.

* * * * *